United States Patent
Szabolcs et al.

(10) Patent No.: US 10,531,945 B2
(45) Date of Patent: Jan. 14, 2020

(54) METHODS AND DEVICES FOR MINIMALLY INVASIVE TRANSCATHETER CORONARY ARTERY BYPASS GRAFTING

(71) Applicants: BOSTON SCIENTIFIC SCIMED, INC., Maple Grove, MN (US); REGENTS OF THE UNIVERSITY OF MINNESOTA, Minneapolis, MN (US)

(72) Inventors: Annamaria Szabolcs, Rochester, MN (US); Jeffrey W. Reineke, Vadnais Heights, MN (US); Andrew D. Bicek, Elk River, MN (US); John R. Ballard, Saint Bonifacius, MN (US); Steven L. Kangas, Woodbury, MA (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 745 days.

(21) Appl. No.: 15/004,322

(22) Filed: Jan. 22, 2016

(65) Prior Publication Data
US 2016/0213462 A1    Jul. 28, 2016

Related U.S. Application Data

(60) Provisional application No. 62/106,535, filed on Jan. 22, 2015.

(51) Int. Cl.
*A61F 2/06* (2013.01)
*A61F 2/958* (2013.01)
*A61M 25/09* (2006.01)

(52) U.S. Cl.
CPC ............ *A61F 2/06* (2013.01); *A61F 2/958* (2013.01); *A61M 25/09* (2013.01)

(58) Field of Classification Search
CPC combination set(s) only.
See application file for complete search history.

(56) References Cited

U.S. PATENT DOCUMENTS

| | | | |
|---|---|---|---|
| 5,431,673 A | 7/1995 | Summers et al. | |
| 2001/0004699 A1* | 6/2001 | Gittings | A61B 17/11 606/153 |
| 2002/0108621 A1* | 8/2002 | Berg | A61B 17/064 128/898 |
| 2002/0138129 A1* | 9/2002 | Armstrong | A61F 2/07 623/1.11 |
| 2003/0028200 A1* | 2/2003 | Berg | A61B 17/0644 606/108 |
| 2003/0074057 A1* | 4/2003 | Rosengart | A61B 17/11 623/1.23 |
| 2011/0313283 A1 | 12/2011 | Kapadia | |
| 2012/0130413 A1 | 5/2012 | Remmerswaal et al. | |

* cited by examiner

*Primary Examiner* — Richard G Louis

(57) ABSTRACT

Systems and methods for performing transcatheter coronary artery bypass grafting procedures are provided. The methods generally involve passing the graft from the aorta to the coronary artery through the pericardial space. The systems include poke-out wires, a coring device, and devices for forming anastomoses at the proximal and distal ends of a vascular graft.

14 Claims, 29 Drawing Sheets

Aortic poke-out device with combined poke-out and capturing wire

METHODS AND DEVICES FOR MINIMALLY INVASIVE TRANSCATHETER CORONARY ARTERY BYPASS GRAFTING

CROSS-REFERENCE TO RELATED APPLICATIONS

This application claims the benefit of priority to U.S. Provisional Patent Application No. 62/106,535 by Szabolcs et al. titled "METHODS AND DEVICES FOR MINIMALLY INVASIVE TRANSCATHETER CORONARY ARTERY BYPASS GRAFTING" and filed Jan. 22, 2015, which application is incorporated by reference in its entirety and for all purposes.

FIELD OF THE INVENTION

This application relates to the field of medical devices and medical procedures. More particularly, the application is related to devices and methods for transcatheter medical procedures.

BACKGROUND

Coronary heart disease ("CHD") is a disease in which the coronary arteries (blood vessels which feed oxygenated blood to the heart) become obstructed by the buildup of lipid-rich plaque. As plaque ages, it may become calcified, permanently narrowing the coronary arteries, or it may contribute to the formation of blood clots, which in turn can partially or fully obstruct the coronary arteries. In both cases, the flow of oxygen-rich blood to the heart is decreased, leading to angina (pain or discomfort in the chest) or heart attack.

There are two common treatments for CHD: angioplasty and coronary artery bypass grafting ("CABG"). Angioplasty is a non-surgical procedure in which a balloon catheter is threaded into a coronary artery and is used to widen obstructions caused by accumulations of plaque. Angioplasty may also involve the placement of a stent within narrowed portions of the coronary artery to improve the flow of blood within those portions. CABG, meanwhile, is the most common form of open heart surgery, in which a section of a healthy blood vessel is harvested from another portion of the body (for instance, the patient's internal mammary artery or a vein taken from the patient's leg) and grafted to form a link between a source of fresh oxygenated blood such as the aorta and the portion of the coronary artery downstream of the blockage. CABG, as currently practiced, involves open heart surgery (thoracotomy) or throacoscopy, and may also involve the use of a heart-lung bypass machine. While CABG is typically necessary in cases of CHD too severe to be treated effectively using angioplasty, the risks and costs associated with the CABG procedure are significantly greater than those presented by angioplasty.

SUMMARY OF THE INVENTION

The present invention, in its various aspects, meets an ongoing need in the field for a CABG procedure with reduced risk and lower cost by providing systems and methods for transcatheter CABG procedures.

In one aspect, the present invention relates to a system for transcatheter vascular grafting that includes first and second catheters, each configured to form a hole in the wall of a blood vessel, a guidewire sized for insertion through a hole in the blood vessel, and a balloon catheter sized and shaped to transport a vascular graft through a blood vessel and the pericardial cavity. The first catheter, in various embodiments of the invention, is sized to be inserted into the aorta of a patient and includes a flexible sheath with first and second ends, at least one end moveable relative to the other, at least two hinges, one or more of which includes an aperture. At the two hinges, the sheath bends to form an angled structure when the first and second ends are moved relative to one another. Within the sheath is slidably disposed a wire configured to penetrate a wall of the aorta or other blood vessel. In some cases, the second catheter is sized for insertion into a coronary artery and includes a dual-lumen sheath which has an open segment defining a gap in the first lumen, a first wire within the first lumen and secured to a distal end of the first lumen, a second lumen with an aperture opposite the gap in the first lumen, and a second wire configured to penetrate a wall of the coronary artery (or other blood vessel), which wire is slidably disposed within the second lumen. In some cases, the system includes a snare with a sheath and a wire slidably disposed within the sheath, the wire having at least one looped structure at its distal end, while in other cases, the snare includes a sheath with an open segment defining a gap in the lumen of the snare and a wire slidably disposed within the sheath such that at least one of the wire and the sheath is capable of forming a looped structure when advanced toward the distal end of the snare. The system also includes, in some cases, a stent configured to form an anastomosis between blood vessels, which stent is disposed on the balloon catheter. Where a stent is used, a clip may also be used to apply radially inward pressure on the graft in order to secure it to the stent. The system also includes, in some cases, a coring tool configured to form a circular aperture in a wall of a blood vessel, which coring tool may include a central anchoring element having a pointed tip and one or more flexible barbs that resist retraction of the central anchoring element. Additionally, the coring tool includes a coring element disposable concentrically about the anchoring element and having a substantially cylindrical body with a distal end defining a circular cutting surface. The system also includes, in some cases, a sealing sheath insertable into a circular aperture in the wall of an aorta, which sheath has a substantially tubular body and one or more sealing elements to form a seal between the sealing sheath and the aorta. The sealing element may be a pair of balloons separated by a space which balloons are configured to contact and seal the wall of the aorta when inflated. Any of the foregoing embodiments of the system can be used in a coronary artery bypass grafting procedure.

In another aspect, the present invention relates to a system for transcatheter vascular grafting that includes first and second catheters, each configured to form a hole in the wall of a blood vessel and each including a wire sized and shaped to be passed through the wall of a blood vessel, a guidewire sized for insertion through a hole in a blood vessel, a snare configured to form a loop, a coring device for forming a circular aperture in the wall of a blood vessel, a stent configured to form an anastomosis between blood vessels, and a balloon catheter sized and shaped to transport the stent and a vascular graft through a blood vessel and a pericardial cavity. The first catheter can include a plurality of hinged structures and at least one wire slidably disposed within one of the hinged structures and capable of being extended through an aperture located in a hinge of one of the hinged structures, as well as a center cap at the distal end of the first catheter which is attached to each of the hinged structures, and a wire tether attached to the center cap which permits the center cap to be moved toward or away from the hinge and the aperture, thereby moving the hinge radially inward or radially outward. These systems can be used for coronary artery bypass grafting, among other things.

In another aspect, the present invention relates to a method of performing a coronary artery bypass grafting procedure that includes the following steps: using catheters, forming a first aperture within a wall of a patient's aorta and a second aperture within a wall of the patient's coronary artery, extending a guidewire through the aorta and into the pericardial cavity and into the coronary artery, passing a vascular graft into the pericardial cavity over the guidewire and forming anastomoses between the coronary artery and the vascular graft and, separately, the vascular graft and the aorta. The step of extending a guidewire from the aorta through the pericardial cavity and into the coronary artery can include the sub-steps of passing a snare through the wall of the aorta into the pericardial cavity, passing a guidewire through the wall of the coronary artery and into the pericardial cavity, capturing the guidewire with the snare, and drawing the snare and the guidewire back through the pericardial cavity and into the aorta. In various embodiments of this method, the snare can include both a sheath and a wire inserted within a lumen of the sheath and secured to the sheath at the distal end of the snare, in which the sheath includes an open segment that defines a gap in the lumen of the sheath such that at least one of the wire and the sheath is capable of forming a looped structure. In these embodiments, the step of capturing the guidewire with the snare includes forming the looped structure with the snare, arranging the guidewire and snare so that the tip of the guidewire passes through the loop, then collapsing the looped structure and, thus, securing the tip of the guidewire between the wire and the sheath of the snare. The method can also include a step of forming a circular aperture within the wall of the aorta, which in turn may involve inserting a central anchoring element through the hole in the aortic wall, which anchoring element has a pointed tip and one or more flexible barbs that resist retraction of the central anchoring element when deployed, then advancing a coring element which can be disposed concentrically over the central anchoring element and which has a substantially cylindrical body and a distal end defining a circular cutting surface.

DRAWINGS

Aspects of the invention are described below with reference to the following drawings in which like numerals reference like elements, and wherein.

Figure 4A:
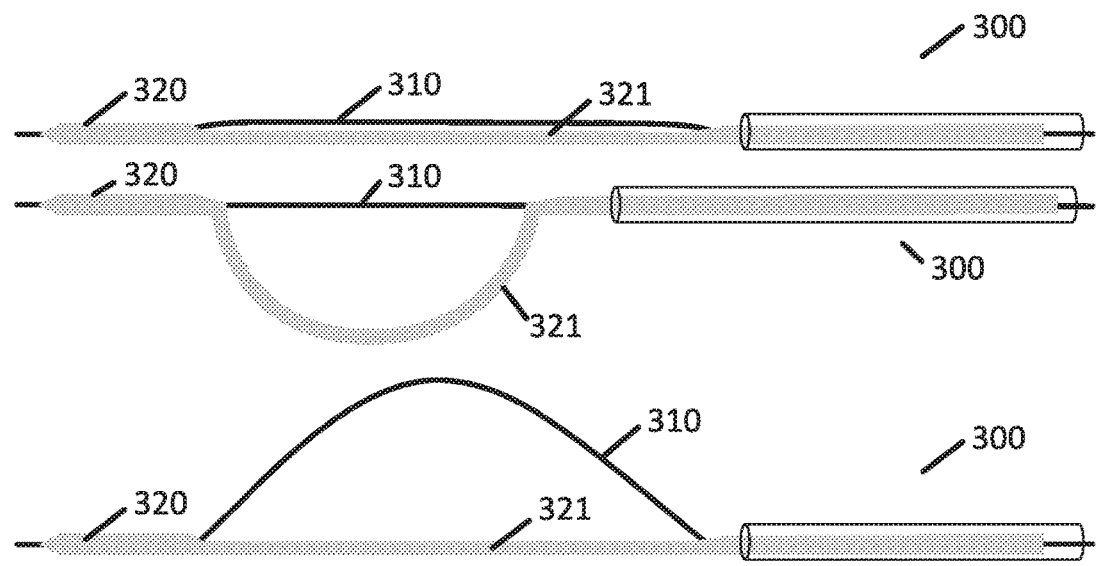
Figure 4B:
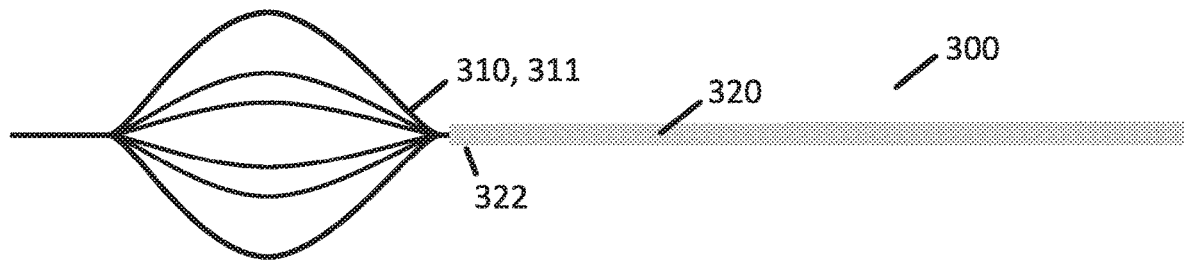
Figure 4C:
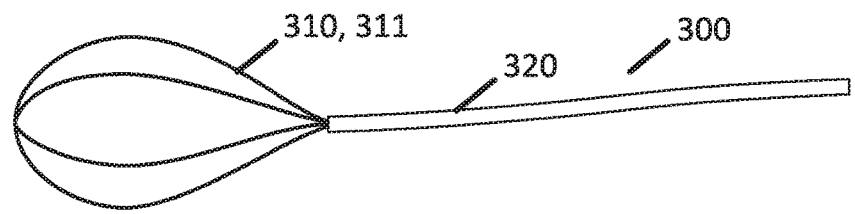
Figure 4D:
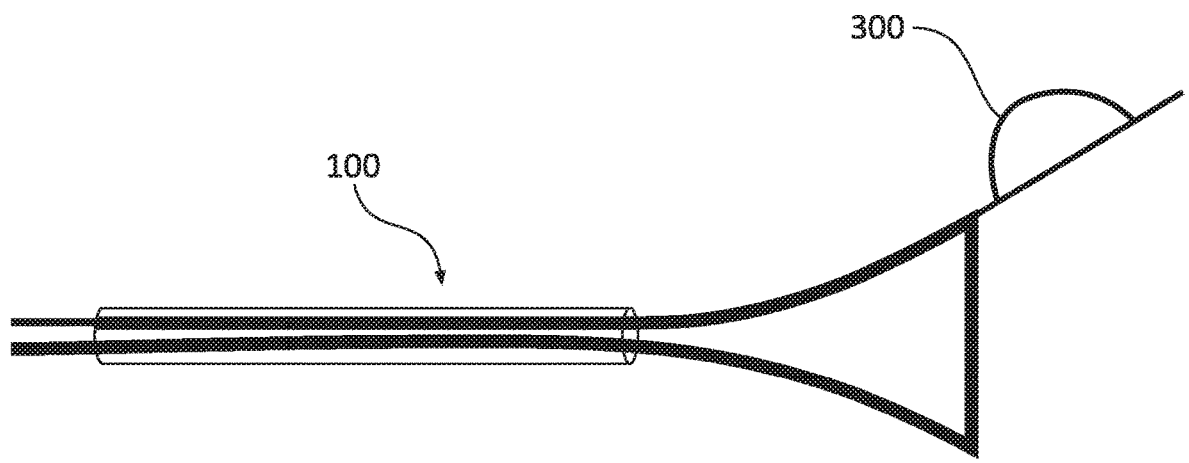

FIGS. 4A and 4B show schematic views of snare wires according to various embodiments of the present invention. FIG. 4C shows a prototype snare wire according to an embodiment of the present invention. FIG. 4D shows a schematic view of a combination poke-out and snare wire according to yet another embodiment of the present invention.

Figure 5A:
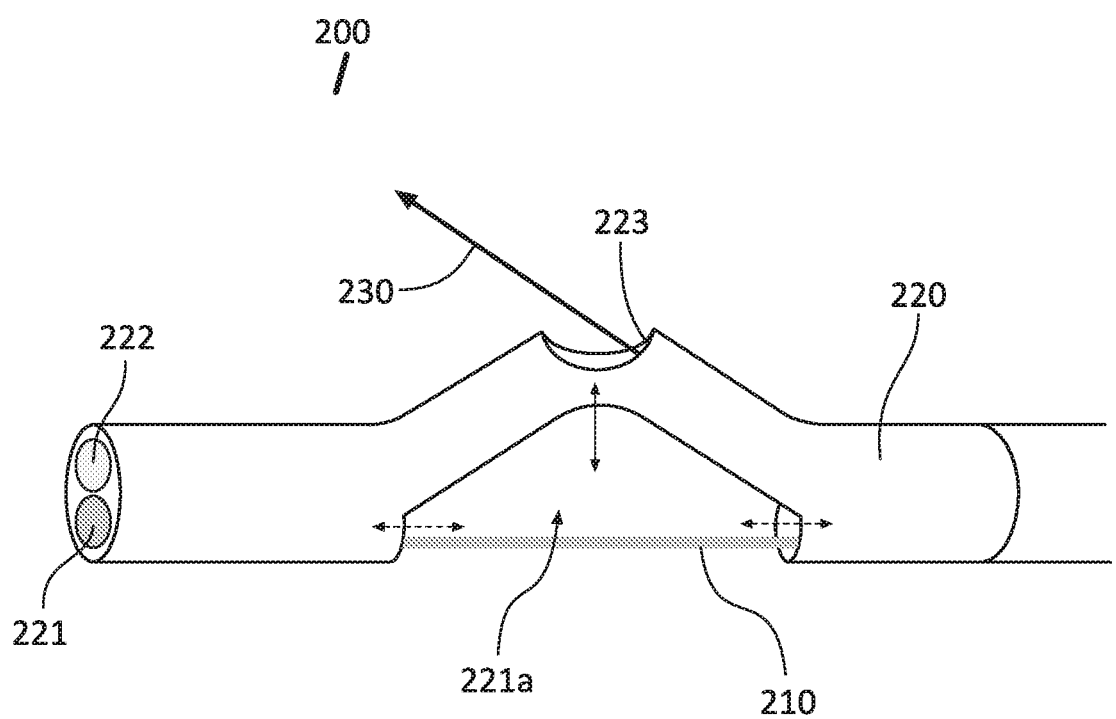
Figure 5B:
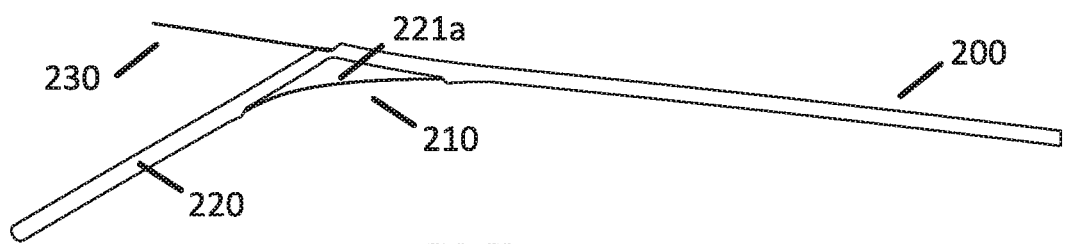
Figure 5C:
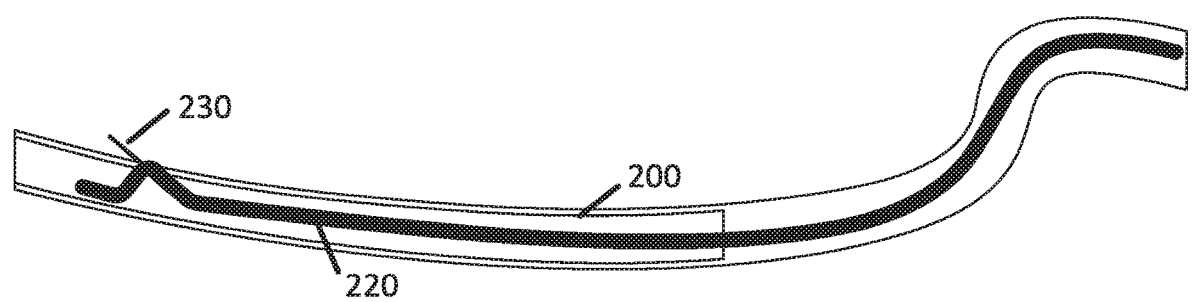
Figure 5D:
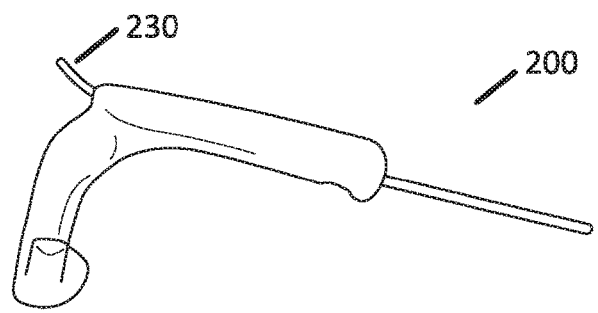

FIGS. 5A and 5B show schematic views of coronary artery poke out device according to an embodiment of the present invention. FIG. 5C shows a schematic view of a coronary wire according to the present invention being used within a coronary artery, while FIG. 5D shows a prototype coronary artery wire with a poke-out structure extended through the wall of a cadaver artery.

Figure 6A:
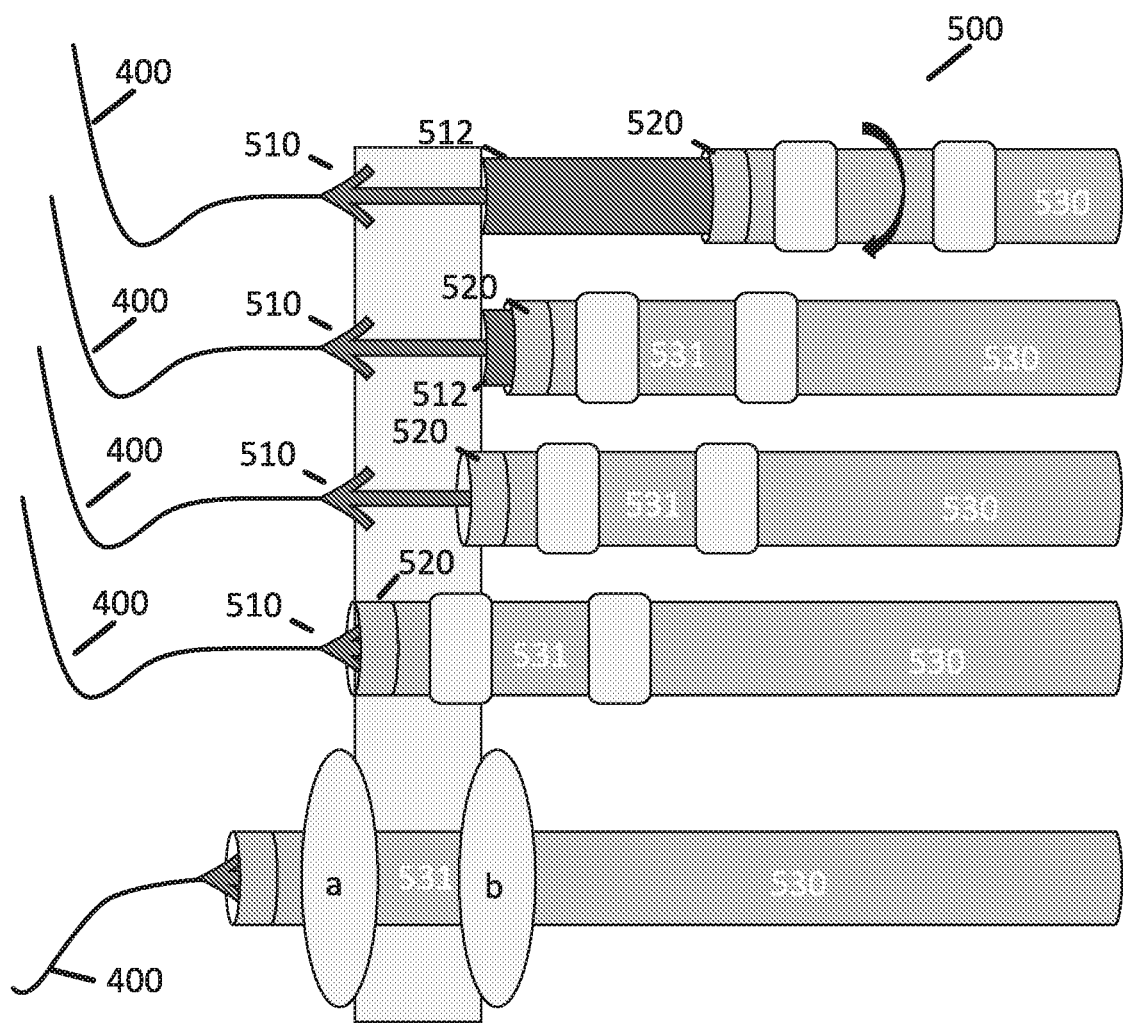
Figure 6B:
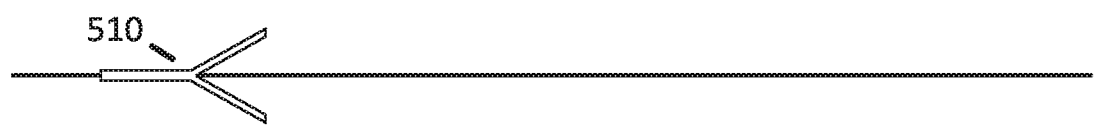
Figure 6C:
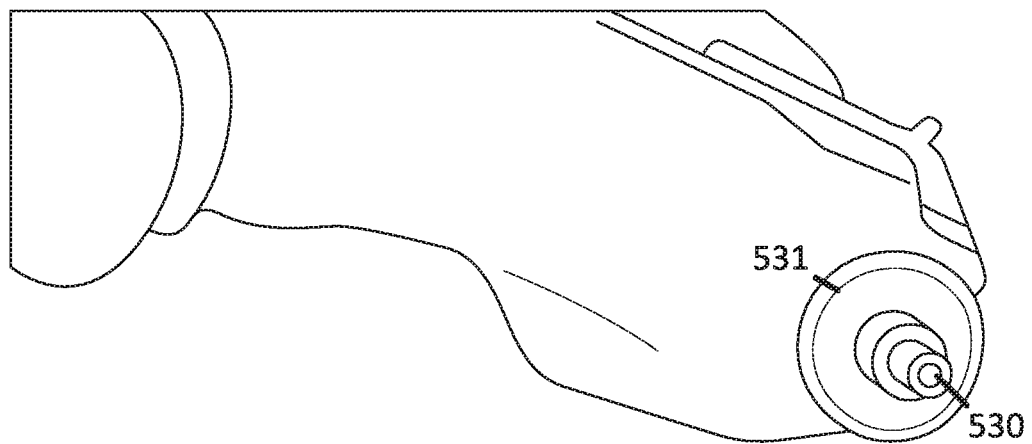
Figure 6D:
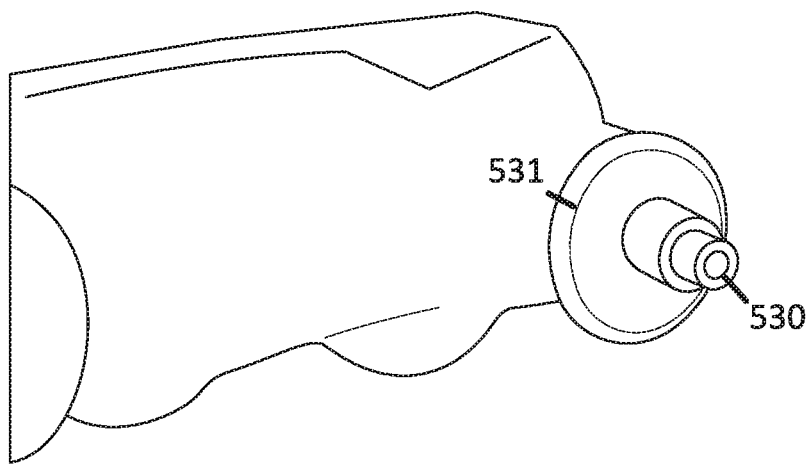

FIG. 6A shows schematic views of an exemplary coring device according to an embodiment of the present invention. FIG. 6B shows a prototype of a central anchoring element, while FIGS. 6C through 6D show views of a prototype sealing sheath in use sealing a cadaver blood vessel in a model of the aorta.

Figure 7A:
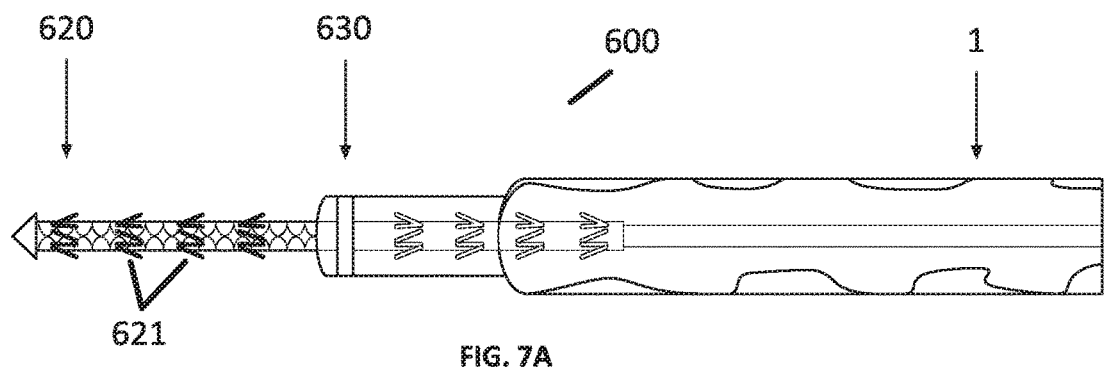
Figure 7B:
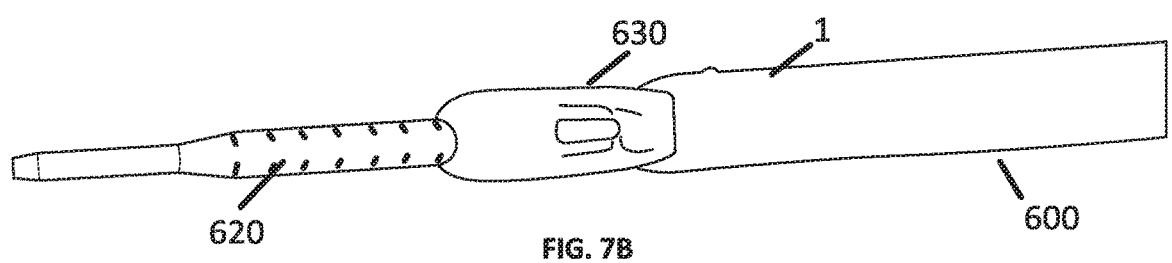
Figure 7C:
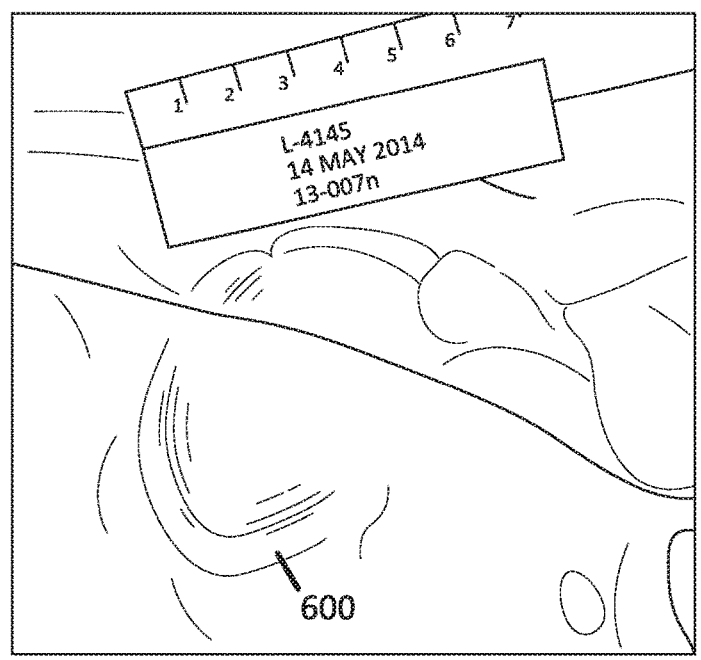
Figure 7D:
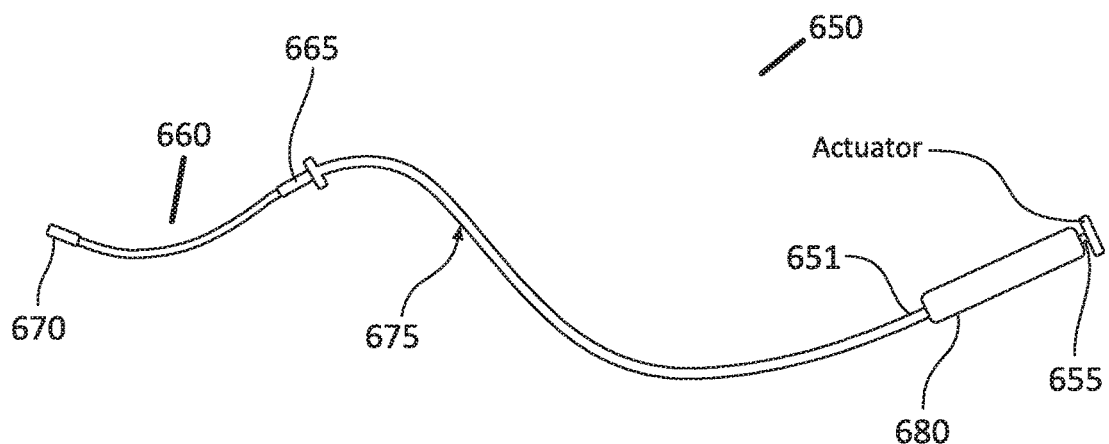

FIG. 7A shows a schematic view of a graft delivery system according to an embodiment of the present invention, while FIGS. 7B through 7C show a prototype graft delivery system including a vascular graft prior to deployment and after deployment in the pericardial cavity. FIGS. 7D through 7H show schematic views of a clip-based graft delivery system according to an alternate embodiment of the present invention.

Figure 8A:
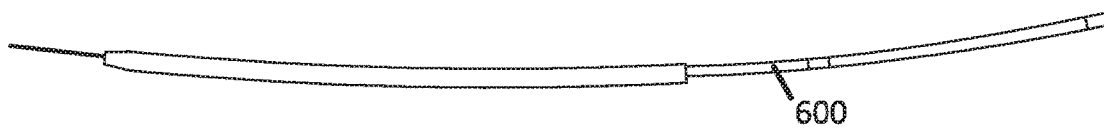
Figure 8B:
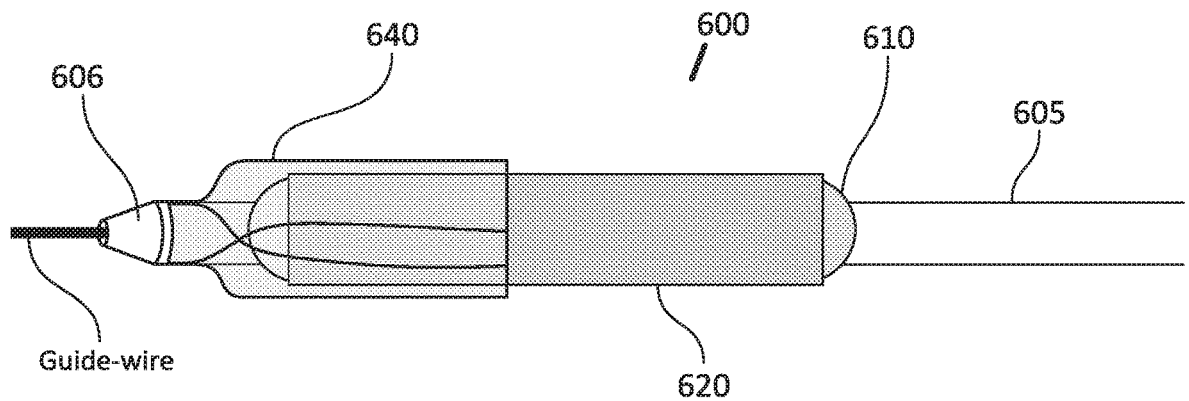

FIG. 8A shows a prototype of a graft delivery system and FIG. 8B shows a schematic depiction of a graft delivery system according to certain embodiments of the present invention. FIGS. 8C through 8G depict the steps in inserting a vascular graft into the coronary artery and forming an anastomosis using a graft delivery system according to the present invention.

Figure 9A:
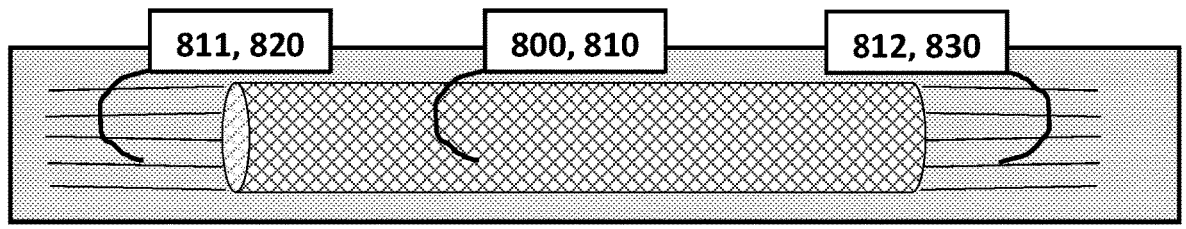
Figure 9B:
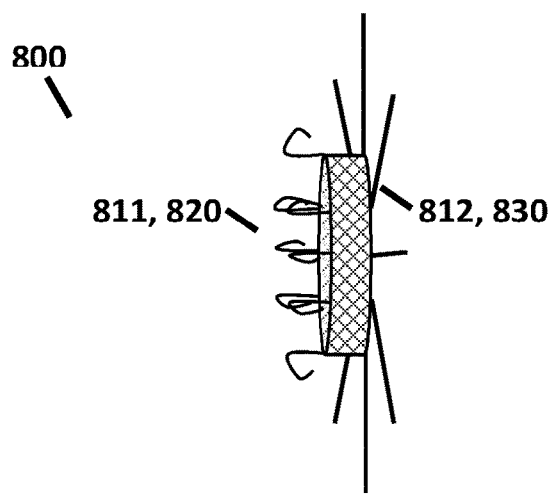
Figure 9C:
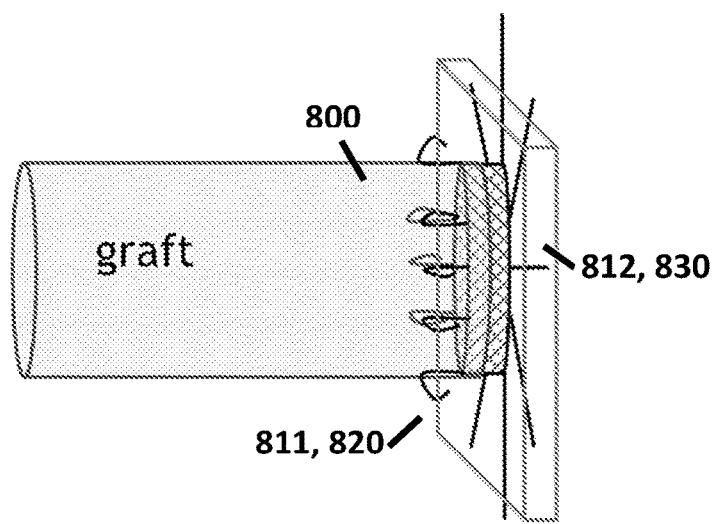

FIGS. 9A through 9C show schematic views of anastomosis devices for use in forming a distal anastomosis between the aorta and the vascular graft, both in un-deployed and deployed configurations.

Figure 10A:
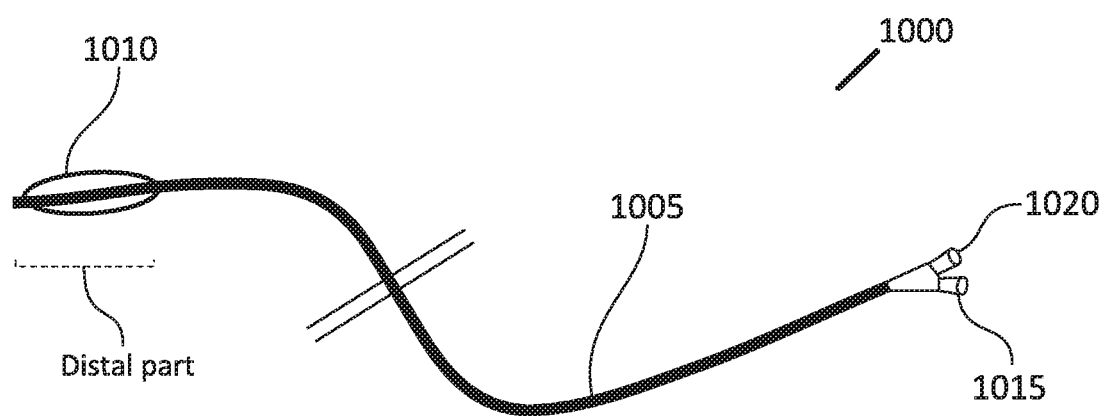
Figure 10B:
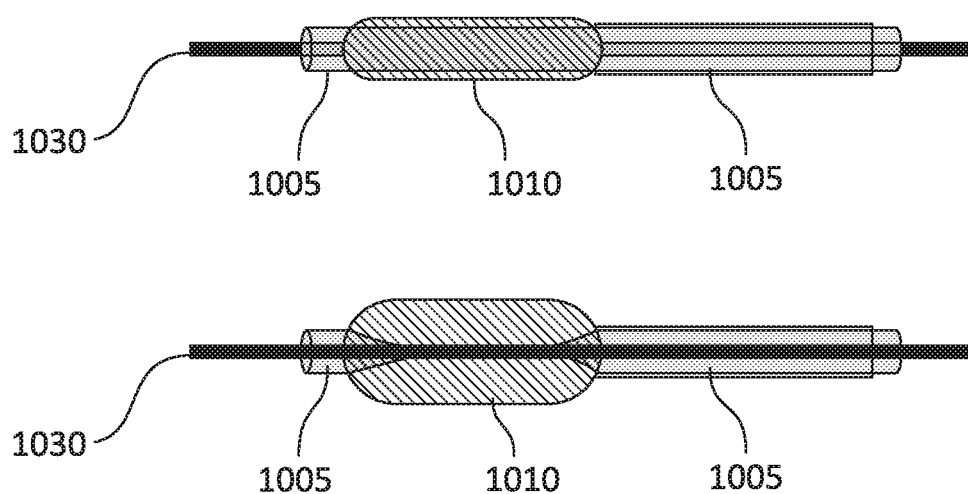

FIGS. 10A through 10B show schematic views of a guidewire-locking catheter according to certain embodiments of the present invention.

Unless otherwise provided in the following specification, the drawings are not necessarily to scale, with emphasis being placed on illustration of the principles of the invention.

DETAILED DESCRIPTION OF THE PREFERRED EMBODIMENTS

Figure 1:
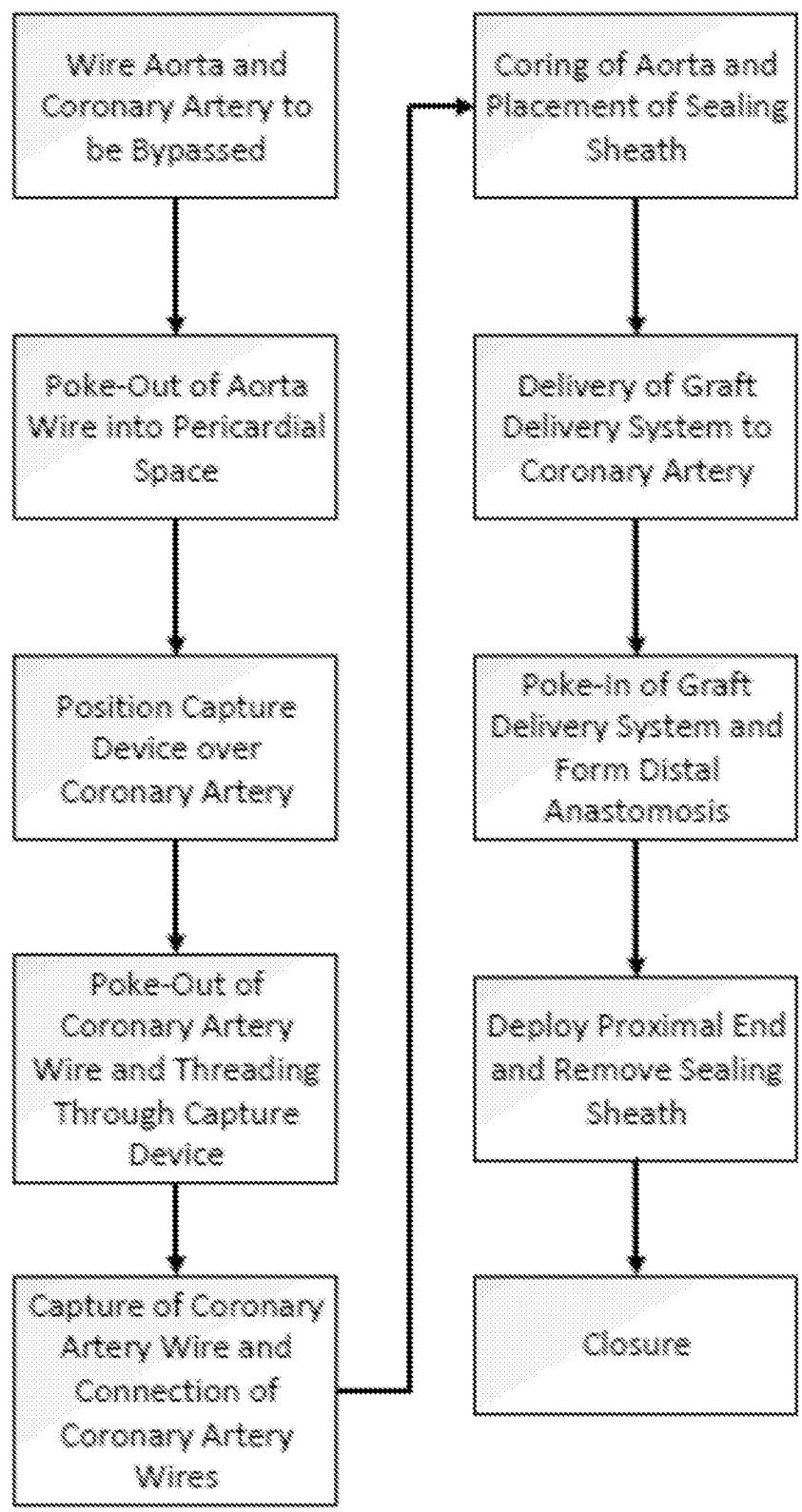
FIG. 1 is a flow chart depicting the steps of a transcatheter CABG procedure according to certain embodiments of the present invention.
Figure 2A:
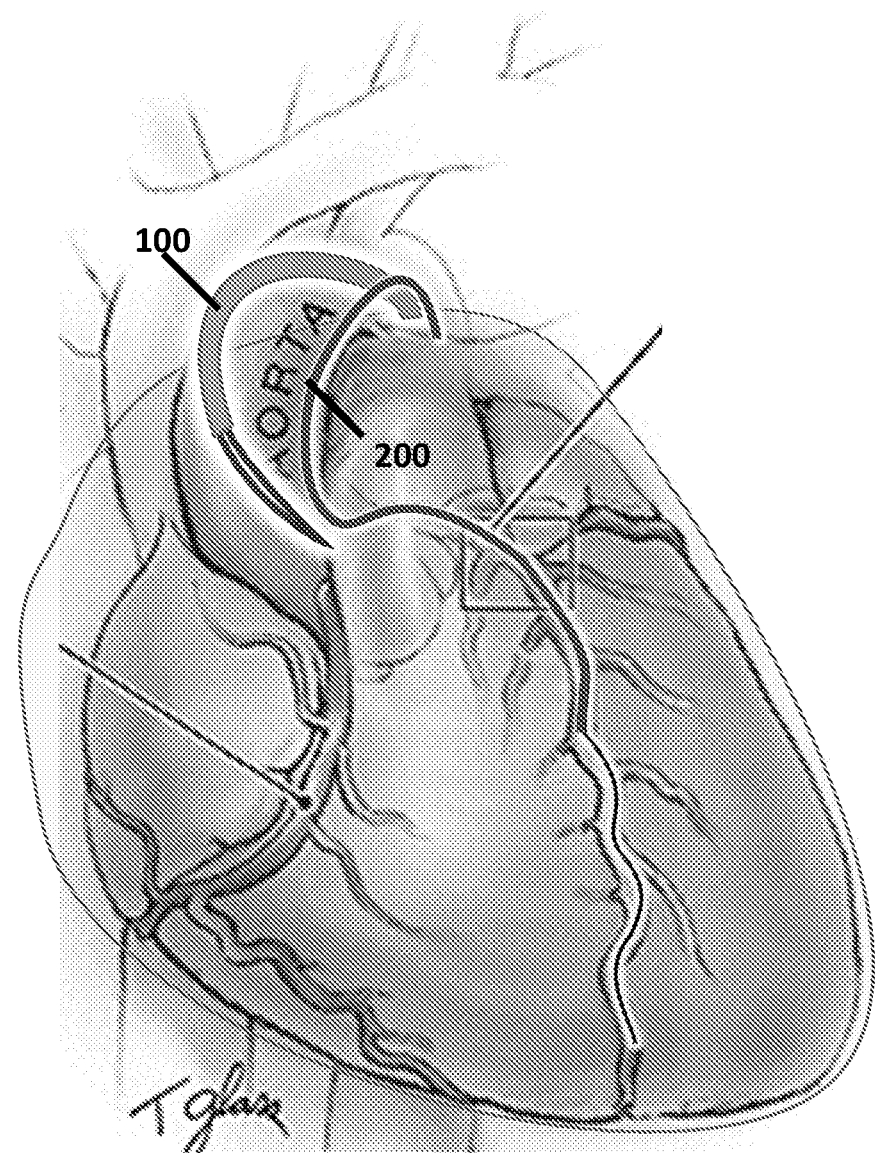
FIGS. 2A through 2I illustrate the steps of a transcatheter CABG procedure according to an embodiment of the present invention
Figure 2B:
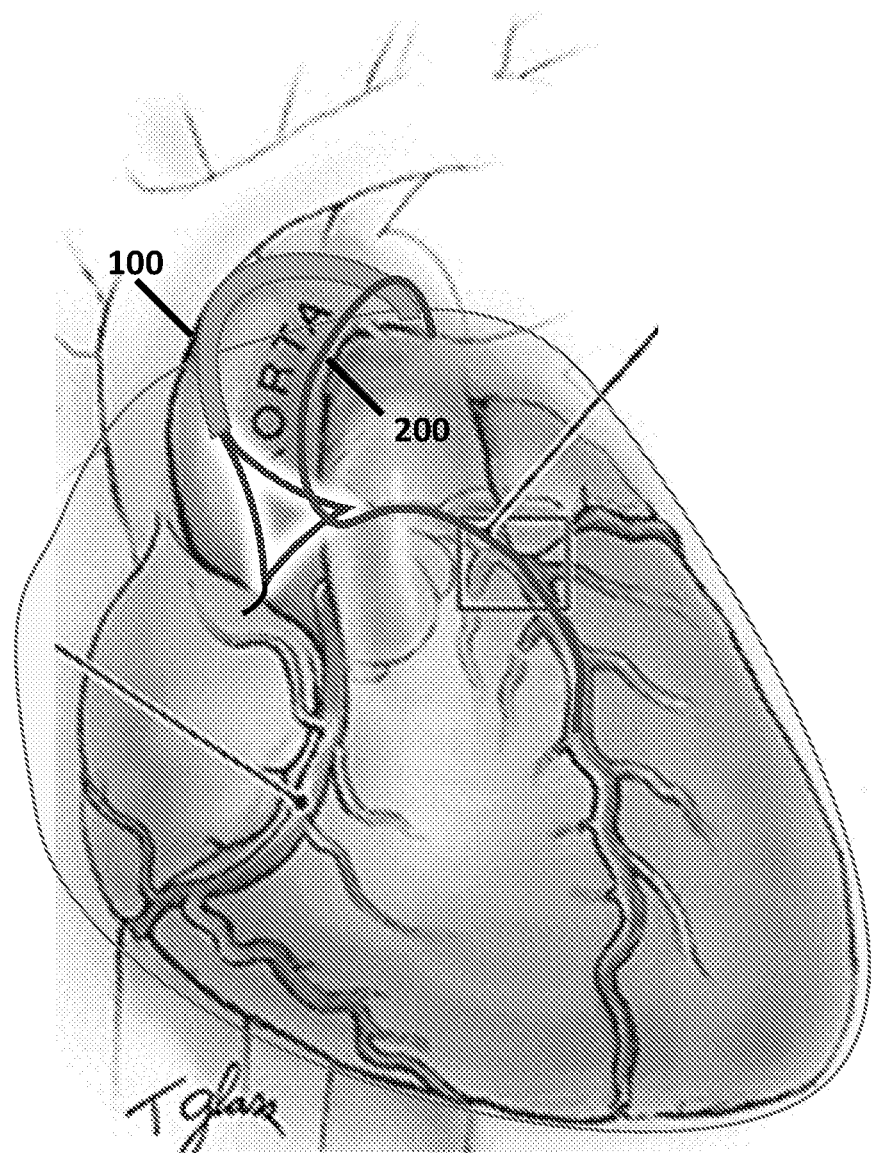

The systems and methods of the present invention are generally directed to CABG procedures which utilize the pericardial cavity (i.e. the space between the inner surface of the parietal pericardium and the visceral pericardium which adheres to the surface of the heart) to pass a vascular graft, anastomosis elements and related components in an "over-the-wire" fashion, eliminating the need for open surgery. The procedure is shown schematically in FIG. 1 and its individual steps are illustrated in FIGS. 2A-I. The procedure begins, as shown in FIG. 2A, with the positioning of two devices: an aortic guidewire and/or catheter 100 (referred to interchangeably as an "aorta wire") is placed within the aorta at a place where a vascular graft 1 will be joined at its proximal end 5, and a coronary artery catheter and/or guidewire 200 (referred to as a "coronary artery wire"), which is inserted into the coronary artery and positioned so that its distal tip is past an obstructed portion of the coronary artery, at a site where the graft will be joined at its distal end. An aortic "poke-out" structure is then delivered to the distal end of the aorta wire 100—in some cases, this is by means of a separate "poke-out" wire which is delivered through an aortic catheter 100, while in other cases the aortic poke-out catheter 100 includes a "poke-out" structure at or near its distal end.

Figure 2C:
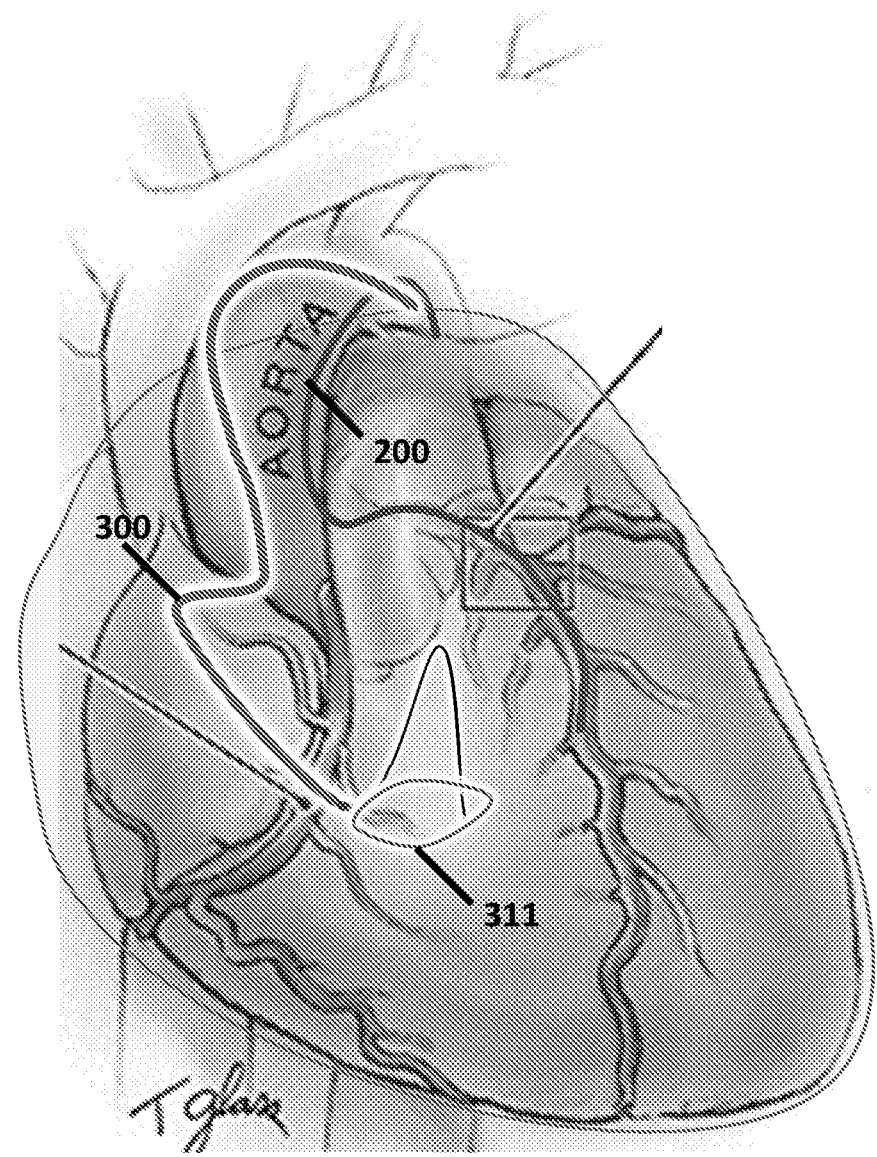
Figure 2D:
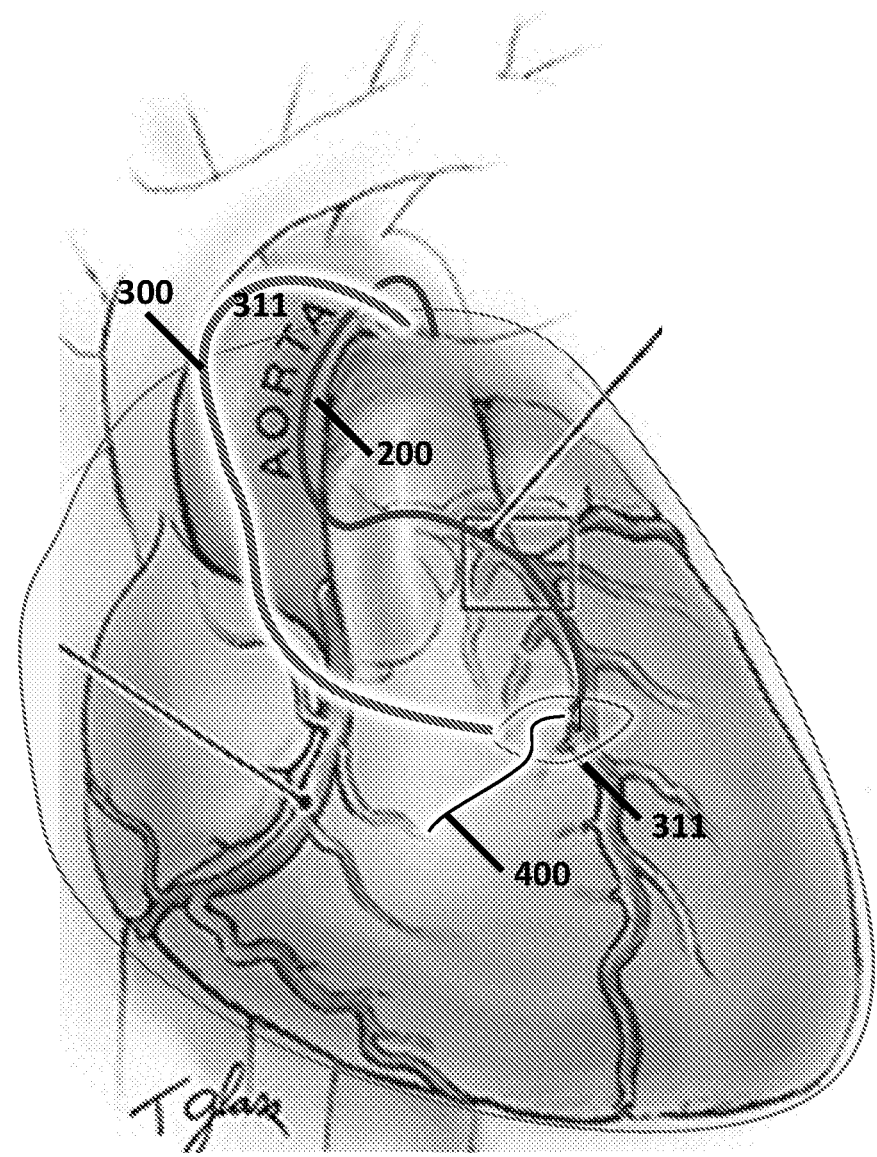
Figure 2E:
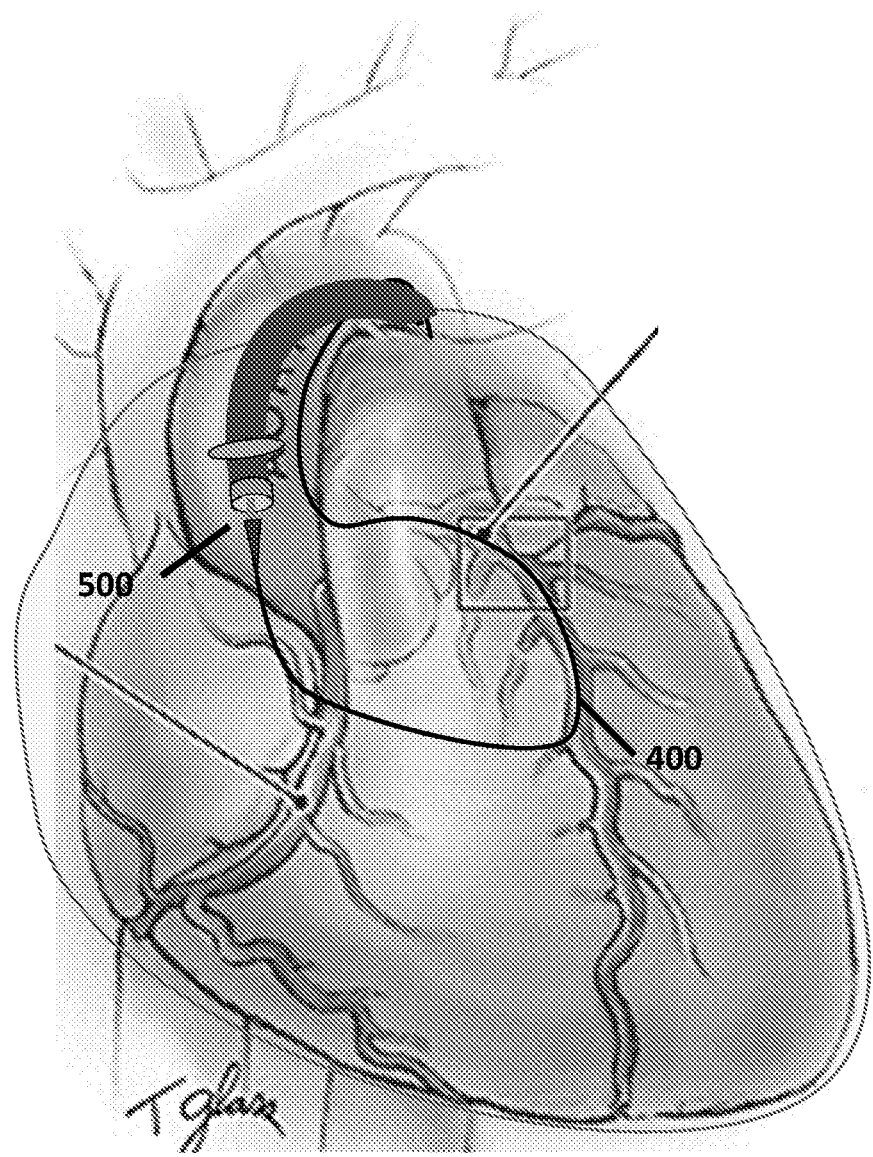
Figure 2F:
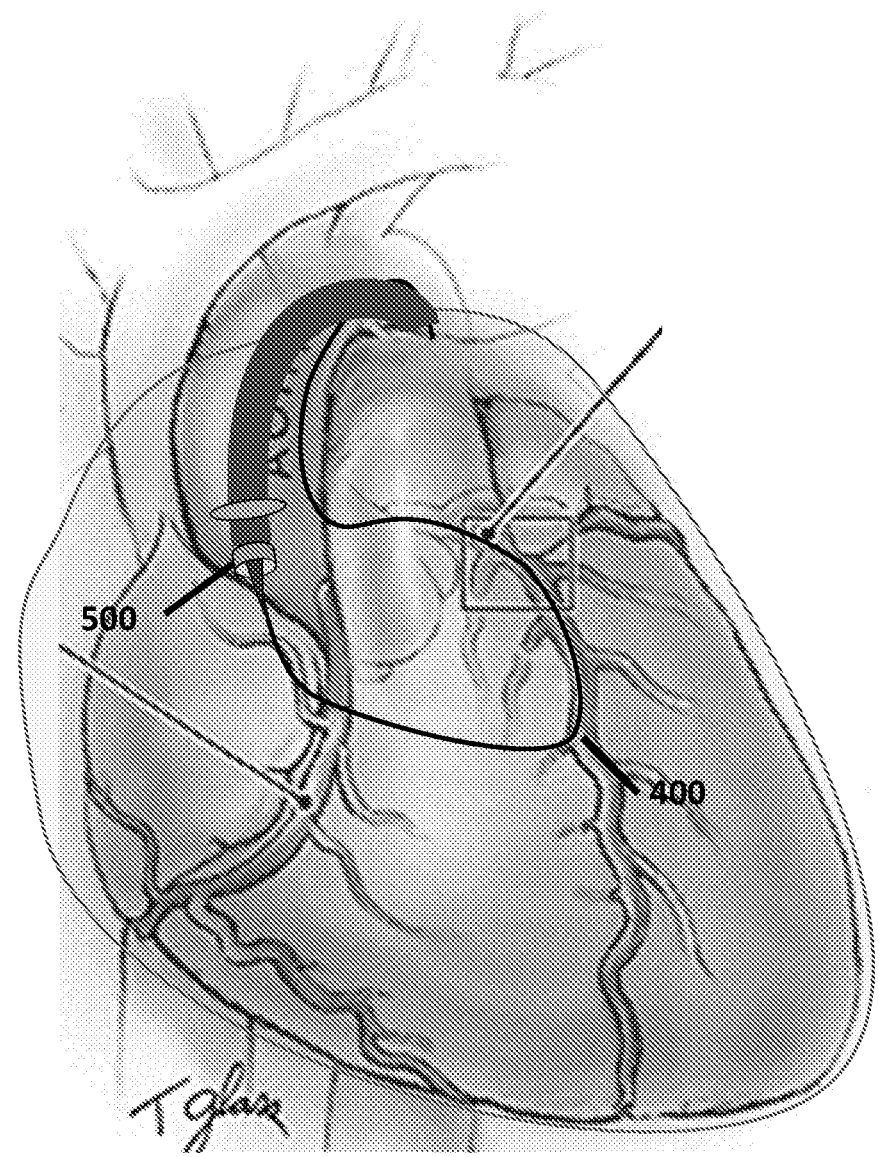
Figure 2G:
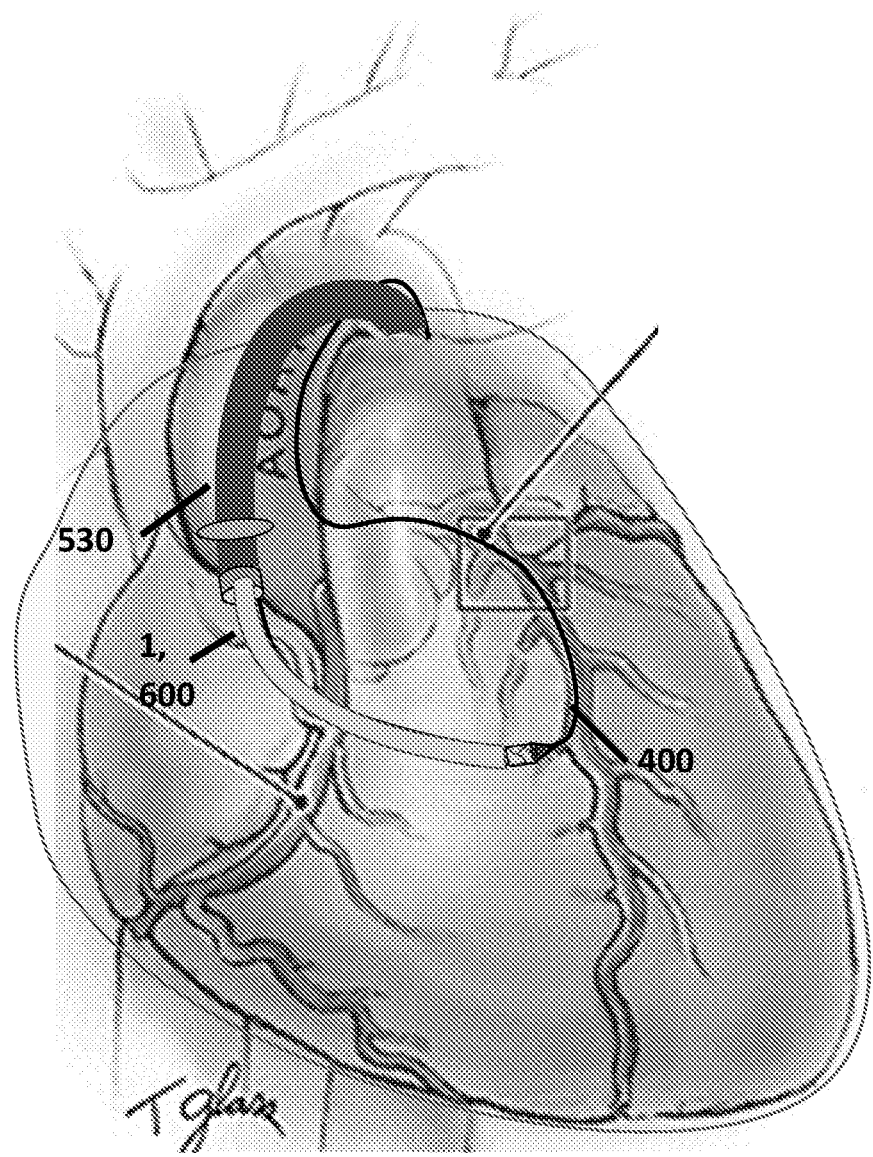

Whatever means are used, the aorta "poke-out" structure is used to form an opening in the aortic wall, through which a snare wire 300 can be inserted as shown in FIG. 2C. A coronary poke out structure is used to form an opening in the coronary artery through which a guidewire 400 is inserted into the pericardial cavity; this is illustrated in FIG. 2D. In some cases, a poke-out device is placed over the coronary artery wire 200, while in other cases the coronary artery wire 200 includes a poke-out structure. The snare wire 300 is used to capture the guidewire 400 and retract it through the pericardial cavity and into the aorta, thereby creating an over-the-wire pathway for placement of the vascular graft 1. To prepare the aorta for placement of the graft, a coring device 500 is inserted over the guidewire 400 and through the wall of the aorta to form a circular arteriotomy (an aperture in the aorta) suitable for anastomosis with the vascular graft (see FIG. 2E). The coring device 500 also includes a sealing sheath 530 having two sealing elements 531 (which can be, for instance, inflatable balloons) which are positioned and deployed (e.g. inflated) adjacent to the inner and outer surface of the aorta to seal the aorta and prevent bleeding through the circular aperture. This is depicted in FIG. 2F.

Figure 2H:
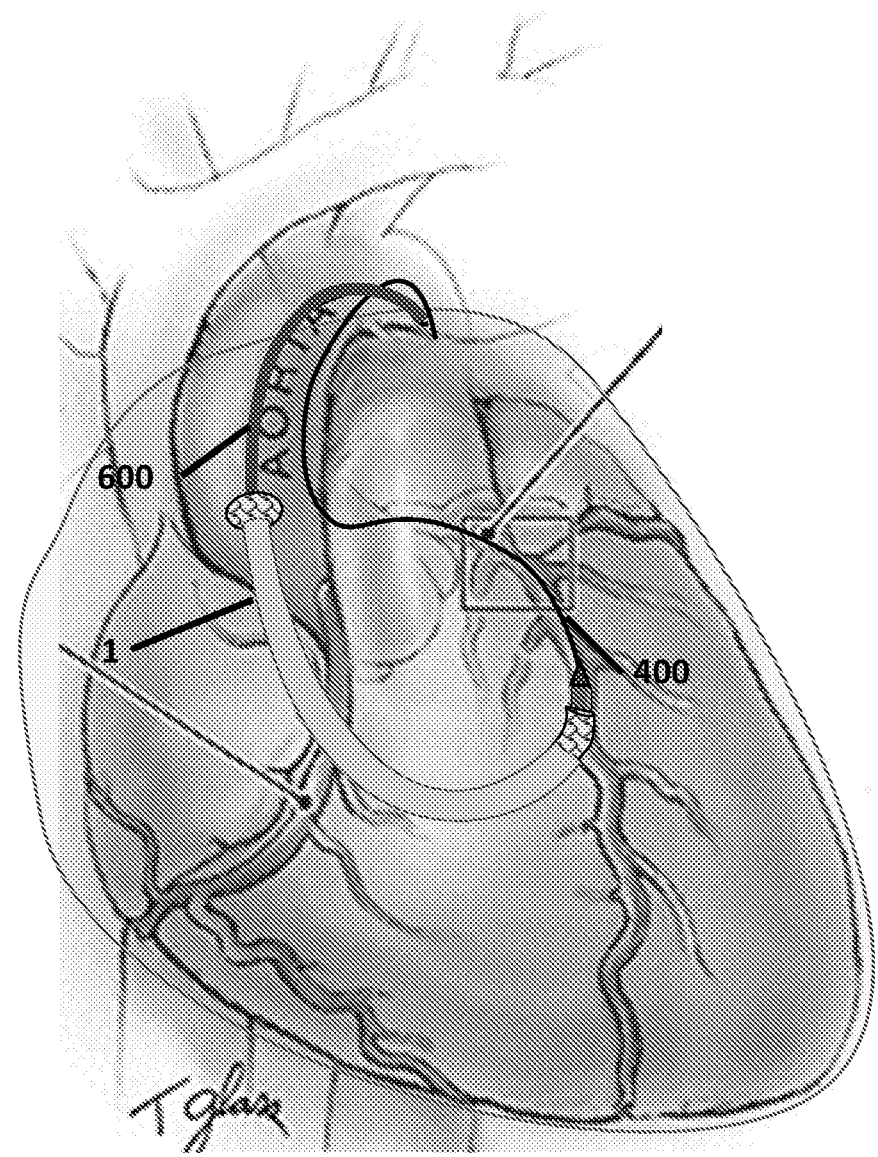
Figure 2I:
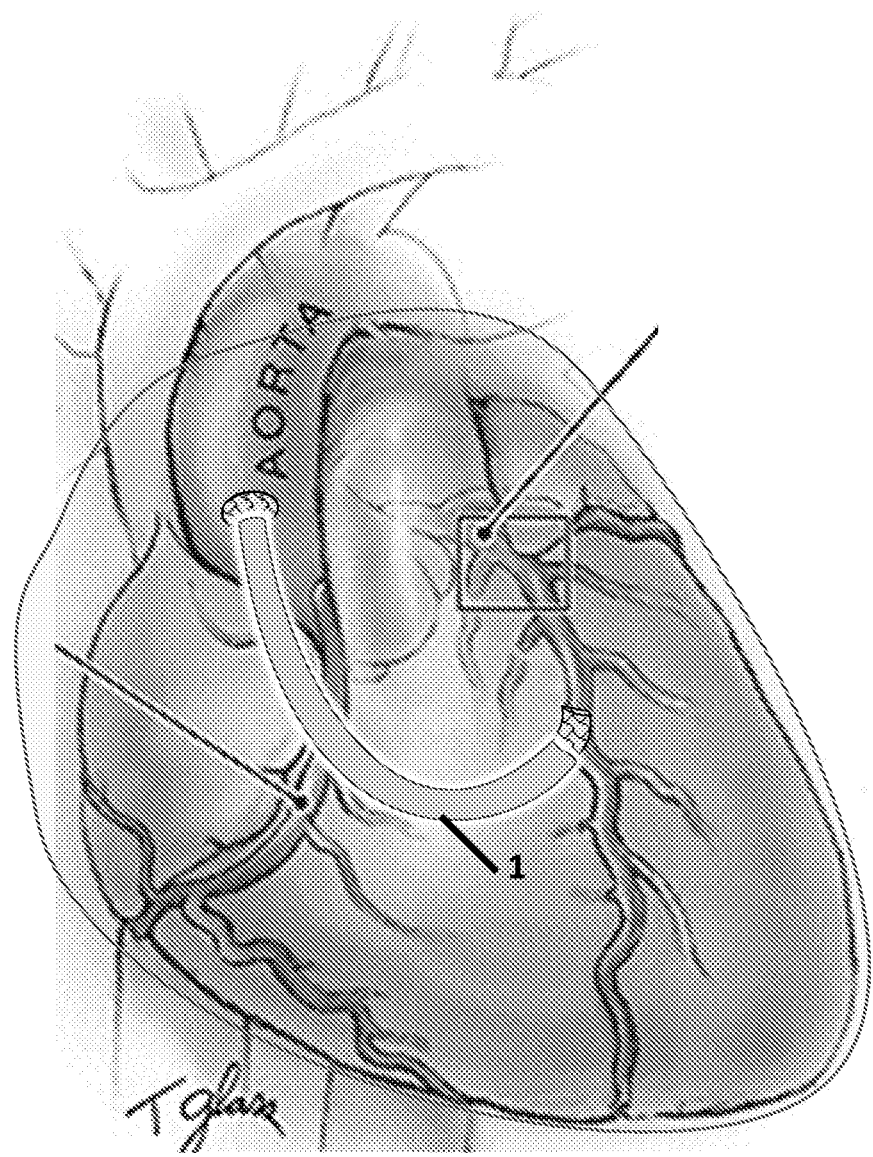

Thereafter, the vascular graft 1 is inserted through the sealing sheath 530 and into the pericardial cavity with the aid of a graft delivery system 600 (FIG. 2G) and positioned so that the distal end of the graft 1 can be anastomosed to the coronary artery while the proximal end can be anastomosed to the aorta, as shown in FIG. 2H. Finally, after anastomoses are formed at each of the proximal and distal ends of the vascular graft 1, the graft delivery device 600 and the guidewire 400 are at least partially retracted, any vascular clamps used during the procedure are opened to permit blood flow through the graft 1, and the procedure is concluded; the final arrangement of the graft 1 and the proximal and distal anastomoses is shown in FIG. 2I.

The method described above involves the use of several catheter-based medical devices, beginning with aortic poke-out catheter 100, which is depicted in FIG. 3. In one embodiment, shown in FIGS. 3A-B, poke-out catheter 100 comprises a flexible sheath 110 and a wire 120 slidably disposed with the sheath. The sheath 110 has first and second ends 111, 112 which are moveable relatively to one another, and two hinges 114, 115 at which the sheath bends to form an angled structure when the first and second ends 111, 112 are brought toward one another. In some embodiments, a segment of the sheath 110 between the two hinges 114, 115 is curved, though in the pictured embodiments it is straight. At least one of the hinges 114, 115 includes an aperture 116 through which the wire can exit the sheath 110. In use, the wire 120 is disposed in the sheath 110 in a position proximal to the hinges 114, 115 and the aperture 116; the sheath is arranged so that one of the hinges 114, 115 lays flat while the other hinge is fully bent, such that it represents the distal-most terminus of the sheath 110. This arrangement is illustrated in the upper panel of FIG. 3A. The poke-out catheter 100 is threaded into the aorta, optionally over a guidewire, such that its distal terminus is adjacent to a site where the proximal anastomosis of the graft 1 will be placed; the ends 111, 112 of the sheath are then moved toward each other (e.g. end closest to the distal-most hinge is drawn backward), to form a triangular structure at the distal end of the sheath 110. In this arrangement, both hinges 114, 115 are adjacent to the walls of the aorta, and the aperture 116 is adjacent to a portion of the aorta that is beneath the pericardial cavity. The wire 120 is then advanced through the aperture 116 and the wall of the aorta and into the pericardial cavity. The lower panel of FIG. 3A illustrates this arrangement schematically, while FIG. 3B shows a prototype aortic poke-out catheter 100 in which the wire 120 has been advanced through the aperture 116.

Figure 3A:
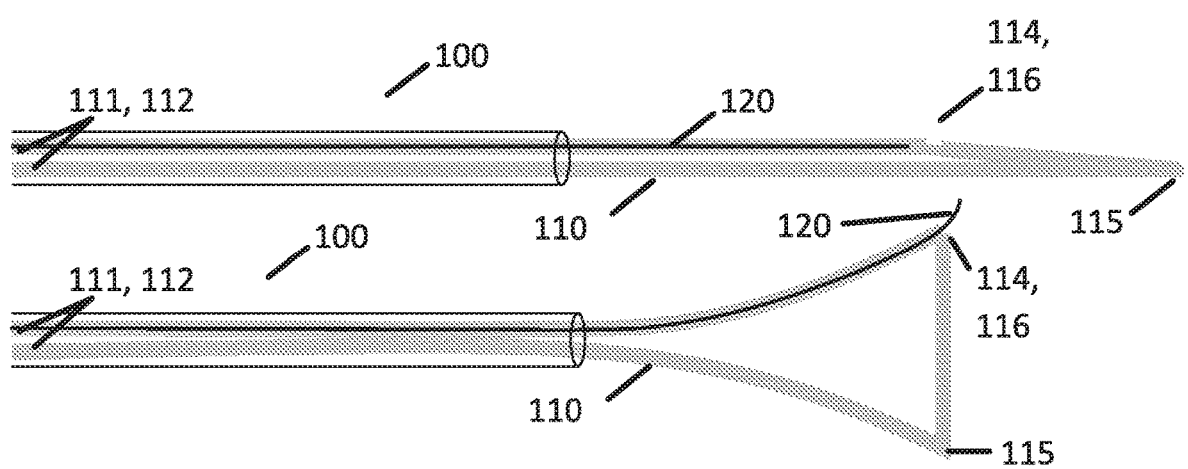
FIGS. 3A through 3E show schematic views and prototypes of aortic poke-out devices according to various embodiments of the present invention.
Figure 3B:
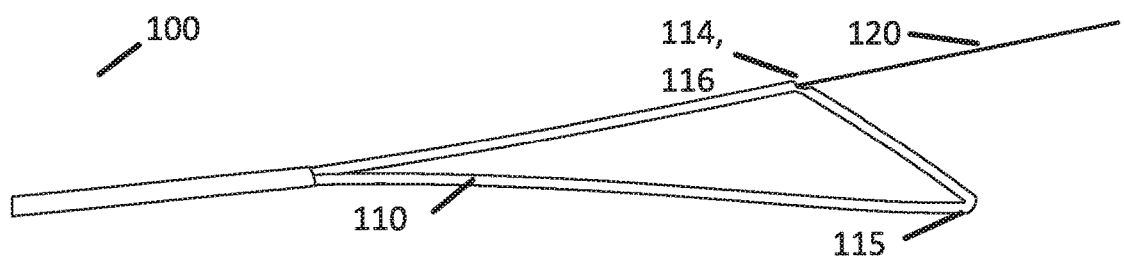
Figure 3C:
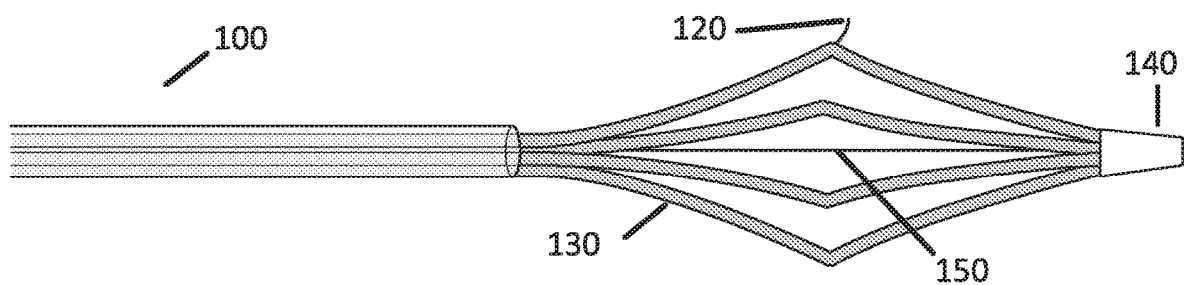
Figure 3D:
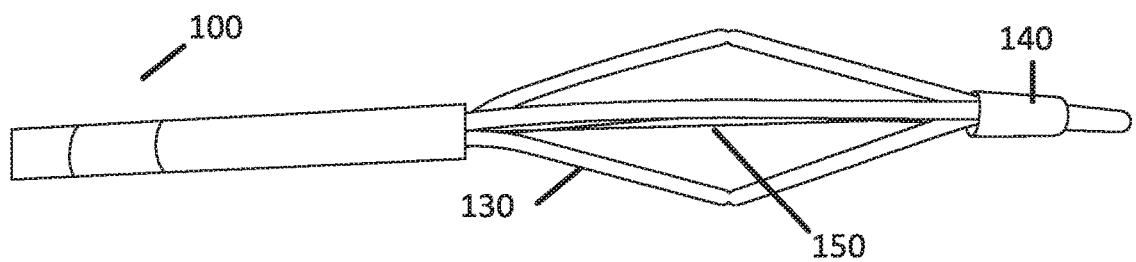

In other embodiments as shown in FIGS. 3C and 3D, the aortic poke-out catheter 100 includes a plurality (e.g. 3, 4, 5, 6 or more) hinged structures 130, and at least one wire 120 slidably disposed within at least one of the hinged structures 130 and capable of being extended through an aperture 131 located in one of the hinges of the hinged structures 130. In these embodiments, each of the hinged structures 130 are secured to one another by a center cap 140 connected to a wire tether 150. By means of the tether 150, the center cap 140 can be advanced away from the hinges, thereby flattening out the aortic poke-out catheter 100, or drawn toward the hinges, thereby extending the hinged structures 130 radially outward so that the hinges, and the at least one aperture 131 are proximate to the wall of the aorta, permitting the wire 120 to poke out of the aorta wall when advanced through the aperture 131 in the same fashion as described above.

Figure 3E:
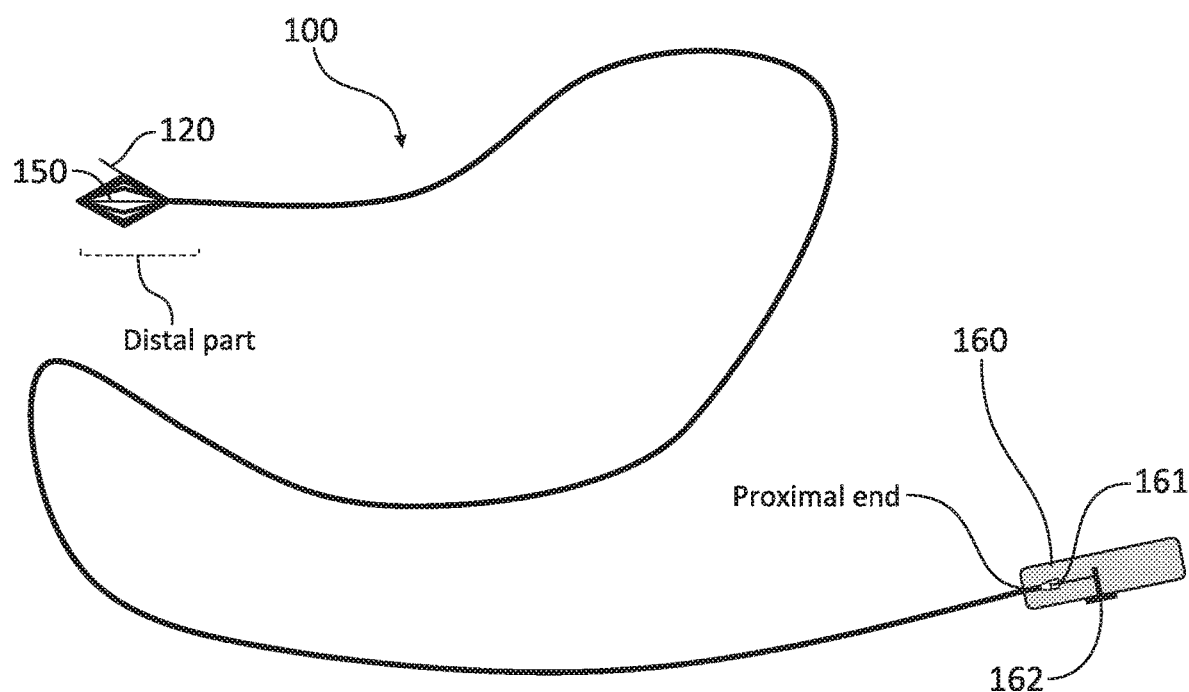

FIG. 3E shows a schematic of an aortic poke-out catheter 100 having a distal end including the poke-out structure (which can include any structure described above, but here shows a structure according to the embodiment of FIGS. 3C-D), and a proximal end including a handle 160 and a port 161 for the poke-out wire 120. The handle 160 also includes an actuator 162 for expanding and collapsing the structure at the distal end, in this case by pushing and/or pulling the wire tether 150.

As discussed above, a snare wire 300 is inserted through the hole in the wall of the aorta created by the aortic poke-out catheter 100. In general, the snare wire 300 can include any structure which is insertable through a narrow-gauge hold in the aorta and which is capable of forming a loop which can be opened and closed so as to capture the guidewire 400. Referring to FIG. 4A, an exemplary snare wire 300 includes a wire 310 and a sheath 320 having an open segment 321 which does not fully enclose the wire 310. At the distal end of the snare wire 300, the wire 310 and the sheath 320 are secured to one another. The distal end also optionally includes a pointed tip to facilitate its exit through the hole in the aortic wall, or it may include an atraumatic tip, e.g. a ball or spring, to prevent its penetration through the pericardium.

In use, the snare wire 300 is advanced through the hole in the aorta and beneath the pericardium in a closed configuration. The snare wire 300 can be opened and closed in multiple ways. First, the snare is opened by advancing the sheath 320 is over the wire 310, allowing the open segment 321 of the sheath 320 to form an arc or loop and creating space between the sheath 320 and the wire 310, as shown in FIG. 4A, middle panel. To close the snare, the sheath 320 is drawn back along the wire. Alternatively or additionally, the snare is opened by advancing the wire 310 within the sheath 320, allowing it to bow outward through the open segment 321 of the sheath 320; the snare is then closed by drawing the wire 310 back through the sheath 320. The snare wire 300 is optionally made of super elastic nitinol.

In other embodiments, such as those shown in FIGS. 4B-C, the snare wire 300 includes a wire 310 with a snare structure 311 at its distal end; the wire is slidably disposed within a sheath 320 having an aperture 322 at or near its distal end. To open the snare in these embodiments, the wire 310 is simply advanced through the aperture 322, and the snare structure 311 expands to form a snare. To facilitate opening of the snare, the snare structure 311 may be formed of a shape memory material such as nitinol. In addition, the snare structure 311 itself may be any structure which can be cinched down to capture the guidewire 400, including a single loop or a plurality of axially-aligned but radially offset loops as shown in FIGS. 4B-C. The snare structure 311 is, in certain embodiments, a snare wire 300 can be deployed through the aortic poke-out wire 100, utilizing the distal tip of the snare wire 300 to poke-out of the aorta and into the pericardial space.

FIG. 4D shows yet another embodiment in which the snare wire and the poke-out device are combined.

We turn next to the coronary artery poke-out catheter 200, an exemplary embodiment of which is shown in FIGS. 5A-D. The coronary artery poke-out catheter 200 includes a pull-wire 210 and a dual-lumen sheath 220 (or, in some cases, a sheath with more than two lumens). The pull-wire 210 is inserted into a first lumen 221 of the sheath 220 and the wire 210 and sheath 220 are secured to one another at the distal end of the coronary artery wire 200. The sheath 220 includes an open segment 221a defining a gap in the first lumen 221; opposite the open segment 221a, the second lumen 222, which is sized and shaped to accommodate the guide wire 400, includes an aperture 223 to permit the guide wire 400 to exit the coronary artery poke-out catheter 200. In use, the coronary artery poke-out catheter 200 is advanced through the coronary artery beyond a stricture or obstruction to a place where the vascular graft 1 will be anastomosed with the coronary artery. The pull-wire 210 is retracted within the first lumen 221, such that the open segment 221a forms a hinge and places the aperture 223 of the second lumen 222 adjacent to the wall of the coronary artery beneath the pericardial cavity. Thereafter, a poke-out wire 230 is advanced through the aperture 223 and out of the wall of the coronary artery into the pericardial cavity. This is illustrated in FIGS. 5A-D. The poke-out wire 230 is captured using the snare wire 300 and drawn back through the pericardial cavity and into the aorta to provide an over-the-wire pathway for delivery of the vascular graft 1. The stiffness of the poke-out wire is selected so that the wire only has enough column strength to poke through the vessel wall when it's supported by the sheath. When the end of the wire exits the vessel and the sheath and enters the pericardial cavity the stiffness of the wire is within a range wherein it does not damage structures in the pericardial space and functions as a regular guide wire.

The next step in the exemplary transcatheter CABG procedure is the coring step, in which a circular arteriotomy suitable for anastomosis is formed within the wall of the aorta. This is facilitated with the use of coring device 500. In the example presented in FIGS. 6A-D, the coring device 500 includes two concentrically-arranged structures—a central anchoring element 510, which is slidably disposed within a coring and sealing sheath 530. Central anchoring element 510 includes a larger-diameter portion 512 proximal to an anchoring element disposed at a distal end of the anchoring element 510. The sealing sheath 530 includes a coring element 520, formed of any suitable material to facilitate penetration and even cutting of the arterial wall, including metal, plastic, etc. The central anchoring element 510 is a tubular structure sized to pass over the guidewire 400. At its distal end, the central anchoring element 510 has a generally pointed or conical structure which is capable of passing through the hole in the wall of the aorta in one direction (e.g. outward into the pericardial cavity), but which resists retraction through the hole in the other direction (e.g. back into the aorta.) In the examples shown in FIG. 6A, and the prototype shown in FIG. 6B, the structure at the distal end of the central anchoring element 510 has a pointed tip and one or more flexible barbs that resist retraction after it has passed through the wall of the aorta.

The sealing sheath 530 is also a substantially tubular body having an outer diameter that is sized to pass through the aperture formed by the coring element 520, but optionally has an outer diameter when unconstrained that is equal to or slightly larger than the aperture, which allows the sealing sheath 530 to help seal the aperture by means of mechanical interference. In addition, in preferred embodiments the sealing sheath 530 includes one or more sealing elements 531 such as flaps or, as shown in FIGS. 6A-D, balloons. As the figures show, the sealing sheath 530 includes, in some cases, two balloons 531a, b separated by a space which is, preferably, sufficiently close in size to a width of the aortic wall to allow the balloons 531a, b to contact and seal the aortic wall when inflated.

In use, the coring device 500 is advanced over the guidewire to the wall of the aorta. The tip 511 of the central anchoring element 510 is advanced through the wall of the aorta and retracted to secure the tip 511 on the outer surface of the aorta. Next, the coring element 520 is placed in contact with the wall of the aorta and advanced; during this step, sufficient tension is applied to the central anchoring element to help draw the coring element 520 through the wall of the aorta, thereby facilitating the formation of a clean arteriotomy. Once the coring element 520 is through, the sealing sheath 530 is advanced through the aperture such that the two balloons 531a, b are on opposite sides of the aortic wall, and are then inflated to form a seal, as shown in the working prototype of FIGS. 6C-D.

Once the sealing sheath 531 is in place, the coring element 520 and the central anchoring element 510 are retracted to prepare the field for delivery of the vascular graft 1. The vascular graft 1 is delivered through the aorta and the sealing sheath 530 over guidewire 400 with the aid of a graft delivery system 600, as shown schematically in FIGS. 7A and 8B, and in prototype form in FIGS. 7B and 7C. The graft delivery system 600 includes a catheter 605 with a guidewire lumen, the catheter 605 optionally having a tapered tip 606, a balloon 610, a stent body 620, and a bands 630 for securing the graft 1 to the graft delivery system 600 and to permit the formation of an anastomosis between the distal end of the graft 1 and the coronary artery. The stent 620 can have any suitable structure, but preferably includes one or more retentive features 621 to ensure it remains in contact with the graft 1 and the wall of the coronary artery when deployed. The retentive features 621 are shown in FIG. 7A as barbs. The band 630 can be any suitable cinching structure, such as the metal clip structure shown in FIG. 7B. A graft delivery system 600 also preferably includes a structure to protect the graft 1 as it is inserted into the coronary artery, such as the half-balloon 640 shown in FIG. 8B, which is positioned over the distal end of the graft 1 and the stent body 620 and is secured to the distal tip of the delivery system 600. Half-balloon 640 prevents the barbs 621 of the stent body 620 from catching on and damaging the wall of the coronary artery during insertion of the graft. The half-balloon 640 is preferably formed of a lubricious, tearable and/or biodegradable or bioresorbable material, to facilitate its removal or degradation following deployment of the stent 620, when it may be pinched between the wall of the coronary artery and the graft 1.

Figure 8C:
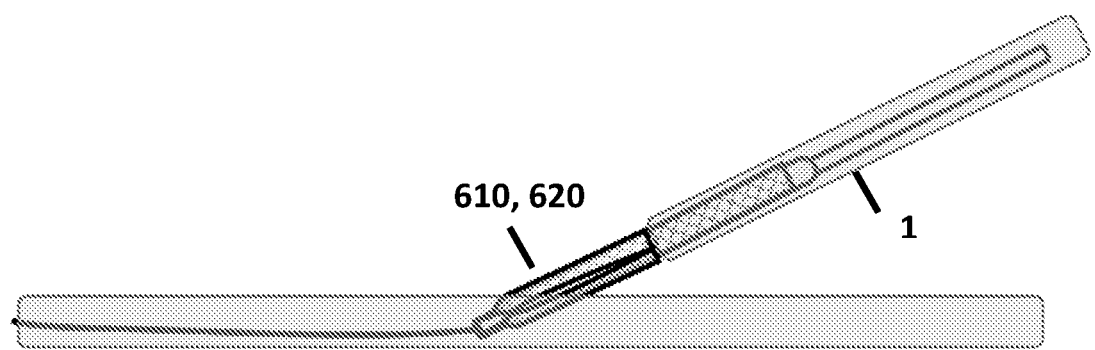
Figure 8D:
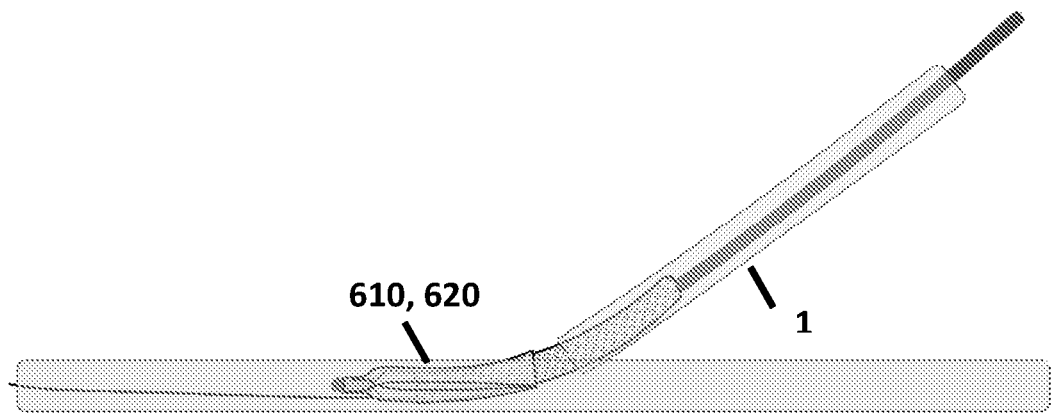
Figure 8E:
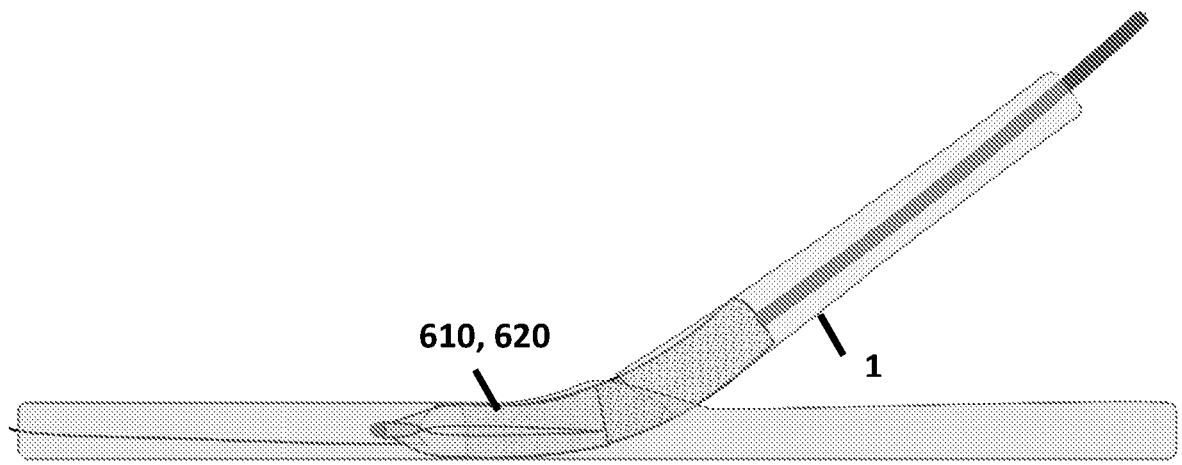
Figure 8F:
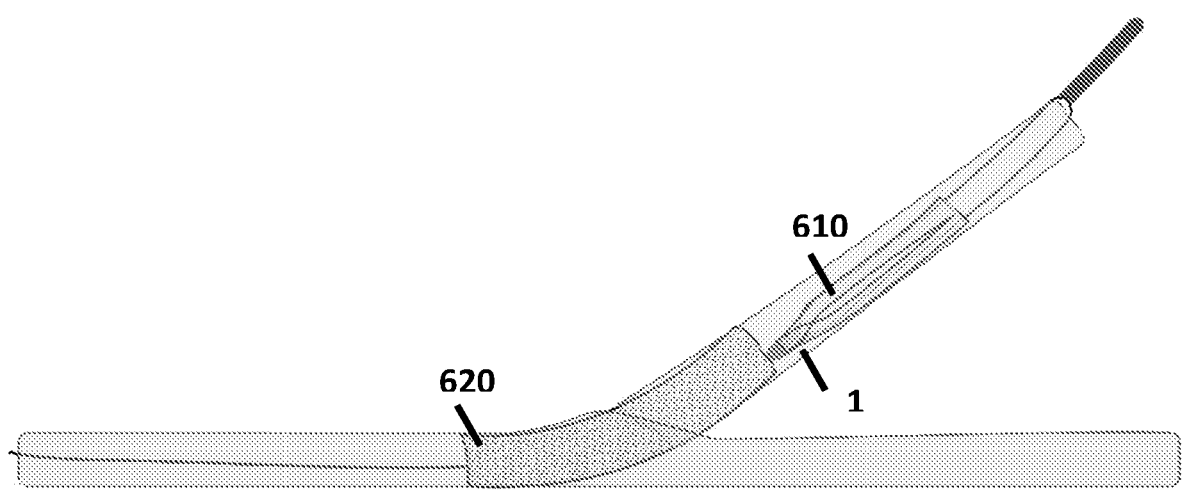
Figure 8G:
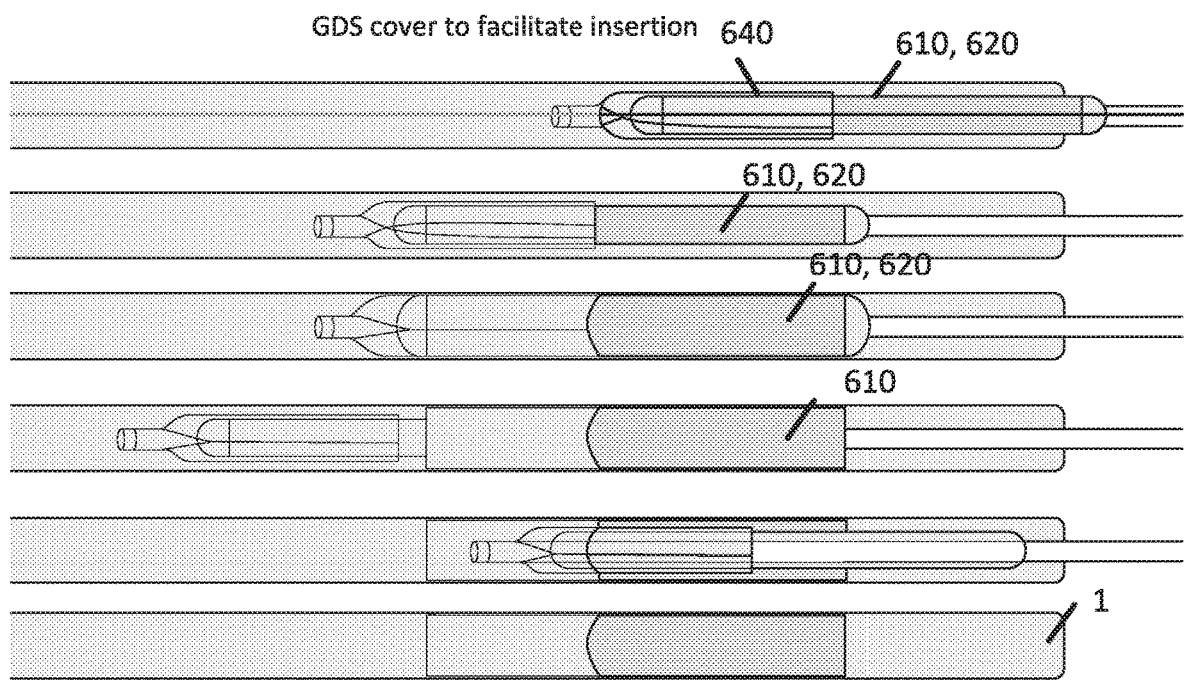

In use the graft 1 is loaded onto the graft delivery system 600 and secured to the stent body 620 by means of the band 630. The graft 1, so attached, is then delivered through the aorta and into the pericardial cavity as shown in FIG. 7C. The distal end of the graft 1 is advanced into the coronary artery as shown in FIG. 8C; thereafter, the balloon 610 is expanded, thereby expanding the stent 620 until it has expanded to a size sufficient to apply a radially-outward oriented retentive force on the wall of the coronary artery. In so doing, a sealed anastomosis is formed between the distal end of the graft 1 and the coronary artery. This process is illustrated in FIGS. 8C-F from a side view and, in a top view, in FIG. 8G.

Figure 7E:
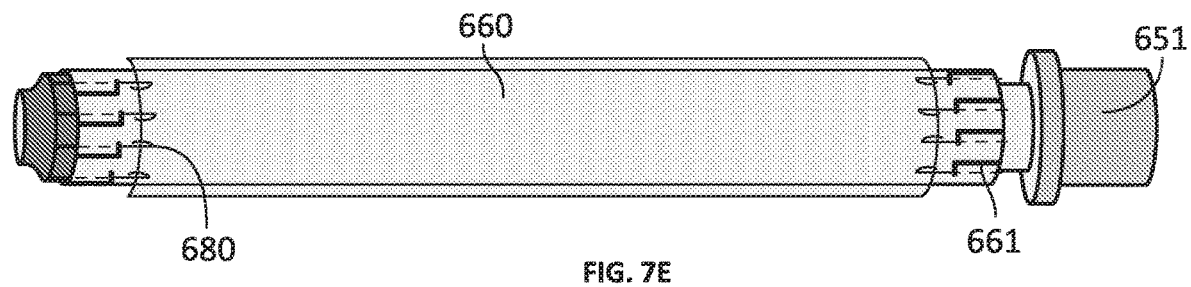
Figure 7F:
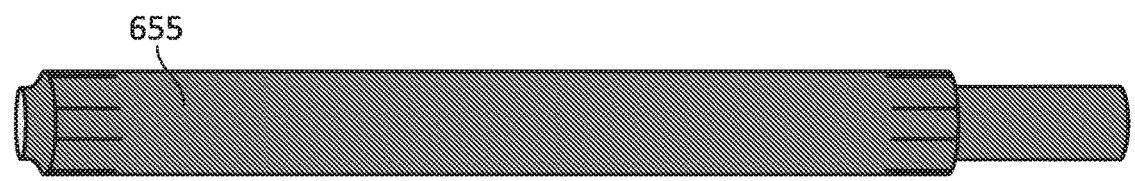
Figure 7G:
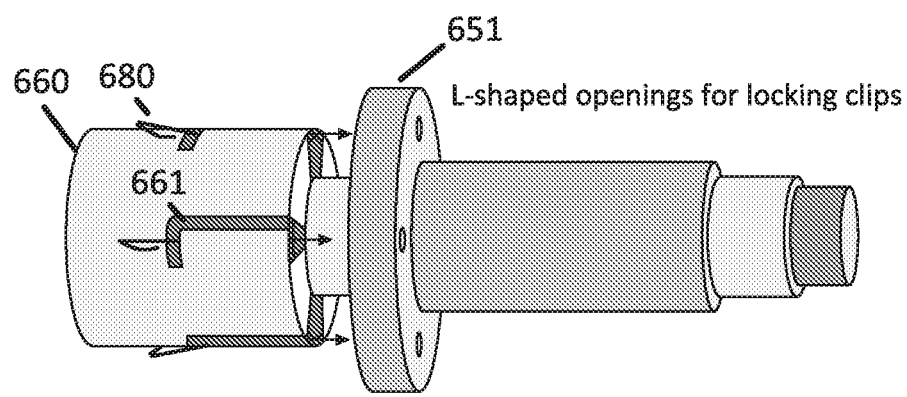

In an alternative embodiment, as shown in FIGS. 7D-H, the graft 1 is delivered using graft delivery system 650 having an elongate catheter body 651 and, at its distal end, inner and outer tubes, 655, 660 disposed concentrically and each extending between proximal and distal securement zones 665, 670. The proximal and distal ends of the outer tube 660 includes a plurality of L-shaped openings 661, each comprising a long portion parallel to the long axis of the system 650 and a short portion angled (e.g. perpendicularly) relative thereto, as shown in FIGS. 7E-G. The L-shaped openings 661 in the proximal securement zone 665 are oriented opposite those in the distal securement zone 670, for reasons discussed below. The outer tube 660 at its proximal (i.e. nearest the user) end steps down to a narrower diameter capable of betting within a flanged overtube 675 slidably disposed over a portion of the catheter body 651 and abutting the proximal securement zone 665. The system 650, which is optionally sized for deployment through an endoscope for applications other than the transvascular CABG procedures disclosed herein, also includes a hand piece 680 which includes an actuator for advancing the inner tube and rotating the outer tube relative to the inner tube.

Figure 7H:
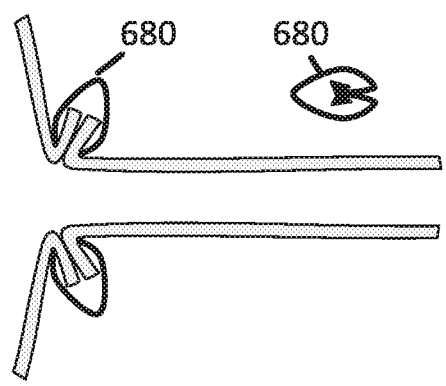

Upon deployment, the graft is held in place by a plurality of shape-memory clips 680 which are deformed so as to extend into the L-shaped openings 661. The clips 680, which are preferably made of nitinol, are shaped to provide an intima to intima alignment and to tightly secure the two vessel walls to each other. As shown in FIG. 7H, this is achieved by means of a clip design that, when unconstrained, which places the two free ends of each clip in close apposition to one another.

In other embodiments, anastomoses between the aorta and the proximal end of the graft 1 are formed by the placement of anastomosis devices, such as the one shown in FIG. 9A-C. The anastomosis devices may have any suitable configuration for an end-to-side anastomosis, but are preferably designed to make conformal contact with an inner surface of the vascular graft and to apply a retentive forces in two directions—radially outward within the vascular graft, and radially inward to ensure that the end of the vascular graft forms a seal with the wall of the aorta. In the exemplary embodiment shown in FIGS. 9A-9C, anastomosis device 800 includes a tubular body 810 having a first, graft facing end 811 and a second, aorta-facing end 812. At the graft facing end 811, the tubular body 810 includes a first plurality of tines 820, which are designed to straighten when the anastomosis device is subjected to a radially-inward force, such as the force applied when the device 800 is within the lumen of a catheter, and then to bend to form a staple-like structure when deployed from the catheter, thereby mechanically connecting the graft-facing end 811 to the graft 1. At the second, aorta facing end 812, the tubular body 810 includes a second plurality of tines 830, which are designed to extend radially outwardly when the device 800 is deployed from a catheter; when deployed, the second plurality of tines 830 draws the end of the graft 1 toward the aorta, facilitating sealing and healing of the anastomosis. In some embodiments, in addition to the second plurality of tines 830, or in lieu of them altogether, the tubular body 810 includes a portion having a larger diameter at the second, aorta-facing end 812.

In some cases, the proximal anastomosis between the graft 1 and the aorta is formed by first inserting the anastomosing device 800 in a sheath or catheter, ensuring that the first and second plurality of tines 820, 830 remain undeployed; the sealing sheath 530 is then withdrawn, and the anastomosing device 800 is deployed so as to form an anastomosis between the proximal end of the graft 1 and the aorta. In other cases, the first plurality of tines 820 are engaged with the proximal end of the graft 1 at the time that the graft 1 is placed on the graft delivery system 600, and the second plurality of tines 830 are constrained until the proximal end is in position and the sealing sheath 530 is removed, at which point the constraint on the second plurality of tines 830 is removed, thereby forming the proximal anastomosis. In these embodiments, the second plurality of tines 830 may be held in a constrained configuration by means of a sheath which is slidably disposed over at least the second end 812 of the tubular body 810 and the second plurality of tines 830.

FIGS. 10A-B depict a device which is used in conjunction with a guidewire in accordance with certain embodiments of the present invention. Wire-locking balloon catheter 1000 is comprised of a compliant (i.e. capable of being pinched closed) multi-lumen catheter body 1005 defining at least a guidewire lumen and an inflation lumen which extend along the length of the catheter body 1005, and a non-compliant balloon 1010 disposed, generally, at or near a distal end of the catheter 1000 and fluidly connected to the inflation lumen of the catheter body 1005. The catheter body 1005 can be any suitable multi-lumen design including the exemplary nested first and second tube design as shown in FIG. 10 B. Cather body 1005 also includes an inflation port 1015 and a wire port 1020 on its proximal end. In use, a guidewire or other elongate instrument 1030 (for example, a poke-out wire as described above) is inserted through the wire port 1020 and the guidewire lumen and extends through the distal end of the wire-locking catheter 1000. When the distal end of the guidewire is located in a position where the user wishes to lock it, the balloon 1010 is inflated by means of a fluid source coupled to the inflation port 1015. Inflation of the non-compliant balloon 1010 compresses the catheter body 1005, thereby locking the wire 1030 into place. To unlock the wire 1030, the non-compliant balloon 1010 is simply deflated and the wire 1030 can be advanced or retracted through the catheter body 1005.

All of the tools discussed above can be made using materials and methods which are standard in the medical device industry. For instance, catheters and other flexible tubular structures, such as the sheaths 120, 210, 310 of the aortic poke-out catheter 100, coronary artery wire 200 and snare wire 300, respectively, as well as the sealing sheath 530, the balloons 531 and 610, etc. can be made of flexible materials currently used to form catheters such as polyurethanes. Structures which must be rigid or somewhat flexible, such as guidewire 400, the central anchoring element 510 or the coring element 520, can be formed using suitable materials, such as stainless steel, while structures which change shape when deployed, such as the first and second plurality of tines 820, 830 can be formed of a shape memory material such as nitinol.

The term "consists essentially of means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system for transcatheter vascular grafting, comprising:
   a first catheter configured for insertion into a first blood vessel of a patient;
   a second catheter comprising a dual-lumen sheath configured for insertion into a second blood vessel of the patient;
   a first wire reversibly disposed within the first catheter, the first wire configured to form a hole in a wall of the first blood vessel;
   a second wire reversibly disposed within the second catheter, the second wire configured to form a hole in a wall of the second blood vessel;
   a guidewire sized for insertion through the hole in the wall of the second blood vessel;
   a balloon catheter sized and shaped to transport a vascular graft through the first blood vessel and a pericardial cavity; and
   wherein the dual-lumen sheath comprises:
      a first lumen, wherein the sheath includes an open segment defining a gap in the first lumen;
      a second lumen sized and shaped to accommodate the guidewire, the second lumen including an aperture opposite the open segment.

2. The system of claim 1, the second catheter further comprising:
   a tether wire; and
      wherein the tether wire is disposed within the first lumen and is secured to the sheath at a distal end of the catheter.

3. A system for transcatheter vascular grafting, comprising:
   a first catheter configured for insertion into a first blood vessel of a patient;
   a second catheter configured for insertion into a second blood vessel of the patient;
   a first wire reversibly disposed within the first catheter, the first wire configured to form a hole in a wall of the first blood vessel;
   a second wire reversibly disposed within the second catheter, the second wire configured to form a hole in a wall of the second blood vessel;
   a guidewire sized for insertion through the hole in the wall of the second blood vessel;
   a balloon catheter sized and shaped to transport a vascular graft through the first blood vessel and a pericardial cavity; and
   a snare reversibly disposed in the first catheter, the snare comprising:
      a sheath; and
      a wire inserted within a lumen of the sheath, wherein the sheath includes an open segment defining a gap in the lumen.

4. The system of claim 1, further comprising a stent configured to form an anastomosis between blood vessels, the stent disposable on the balloon catheter.

5. The system of claim 4, further comprising a clip configured to apply a radially inward pressure on a vascular graft, thereby securing the vascular graft to the stent.

6. The system of claim 1, further comprising a coring tool configured to form a circular aperture within a wall of a blood vessel.

7. The system of claim 6, wherein the coring tool includes:
   a central anchoring element having a pointed tip and one or more flexible barbs that resist retraction of the central anchoring element; and
   a coring element disposable concentrically about the central anchoring element, the coring element having a substantially cylindrical body, the coring element having a distal end defining a cutting surface with a circular cross section.

8. The system of claim 1, further comprising a sealing sheath insertable into a circular aperture in a wall of an aorta, the sealing sheath having a substantially tubular body and having one or more sealing elements to form a seal between the sealing sheath and the aorta.

9. The system of claim 8, wherein one or more of the sealing elements includes a pair of balloons separated by a space, wherein the balloons are configured to contact and seal the wall of the aorta when inflated.

10. A system for transcatheter vascular grafting, comprising:
    a first catheter with a first wire disposed therein, the first wire configured to form a hole in a wall of a first blood vessel;
    a second catheter with a second wire disposed therein, the second wire configured to form a hole in a wall of a second blood vessel;
    a guidewire sized for insertion through the hole in the wall of the second blood vessel;
    a snare configured to form a loop;
    a coring device configured to form a circular aperture within the wall of the first blood vessel;
    a sealing sheath;
    a stent configured to form an anastomosis between the first and second blood vessels; and a balloon catheter sized and shaped to transport the stent and a vascular graft through one of the first or second blood vessels and a pericardial cavity wherein the first catheter further comprises:
a plurality of hinged structures; and
at least one wire slidably disposed within at least one of the hinged structures and configured to extend through an aperture located in a hinge of one of the hinged structures.

11. The system of claims 10, wherein the first catheter includes:
a center cap at a distal end of the first catheter, the center cap secured to each of the hinged structures; and
a wire tether attached to the center cap and configured to move the center cap toward or away from the hinge and the aperture, thereby moving the hinge radially outward or inward, respectively.

12. The system of claim 1, wherein the first blood vessel is an aorta of the patient and the second blood vessel is a coronary artery of the patient.

13. The system of claim 10, wherein the first blood vessel is an aorta of the patient and the second blood vessel is a coronary artery of the patient.

14. The system of claim 3, wherein the wire is secured to the sheath at a distal end of the snare, and wherein at least one of the wire and the sheath is capable of forming a looped structure when advanced toward the distal end of the snare.

\* \* \* \* \*